(12) United States Patent
Shah et al.

(10) Patent No.: US 11,406,830 B2
(45) Date of Patent: Aug. 9, 2022

(54) HALL SENSOR CIRCUIT FOR MAGNETIC FIELD DETECTION IN IMPLANTABLE MEDICAL DEVICE

(71) Applicant: Medtronic, Inc., Minneapolis, MN (US)

(72) Inventors: Jalpa S. Shah, Maple Grove, MN (US); Robert W. Hocken, Jr., Scottsdale, AZ (US); Joel Sivula, White Bear Lake, MN (US); Wesley A. Santa, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 658 days.

(21) Appl. No.: 16/328,587

(22) PCT Filed: Jul. 18, 2017

(86) PCT No.: PCT/US2017/042595
§ 371 (c)(1),
(2) Date: Feb. 26, 2019

(87) PCT Pub. No.: WO2018/044408
PCT Pub. Date: Mar. 8, 2018

(65) Prior Publication Data
US 2021/0275822 A1    Sep. 9, 2021

Related U.S. Application Data

(60) Provisional application No. 62/383,259, filed on Sep. 2, 2016.

(51) Int. Cl.
*A61N 1/37* (2006.01)
*A61N 1/05* (2006.01)
*A61N 1/36* (2006.01)
*A61N 1/39* (2006.01)
*G01R 33/07* (2006.01)

(52) U.S. Cl.
CPC ......... *A61N 1/3718* (2013.01); *A61N 1/0534* (2013.01); *A61N 1/36125* (2013.01); *A61N 1/36142* (2013.01); *A61N 1/3925* (2013.01); *G01R 33/072* (2013.01); *A61N 1/36189* (2013.01)

(58) Field of Classification Search
CPC .............. A61N 1/36189; A61N 1/3925; A61N 1/36142; A61N 1/36125; A61N 1/0534; A61N 1/37818; G01R 33/072
See application file for complete search history.

(56) References Cited

U.S. PATENT DOCUMENTS 6,621,334 B2   9/2003   Ausserlechner et al.
6,674,322 B2   1/2004   Motz
8,518,734 B2   8/2013   Whig et al.
(Continued)

OTHER PUBLICATIONS

International Search Report and Written Opinion of International Application No. PCT/US2017/042595, dated Oct. 19, 2017, 13 pp.

*Primary Examiner* — Joseph M Dietrich
(74) *Attorney, Agent, or Firm* — Shumaker & Sieffert, P.A.

(57) ABSTRACT

Techniques are described for magnetic field detection using a plurality of Hall sensors and chopper-amplifier circuit. Determination that a magnetic field is present from measurement from one of the Hall sensors may trigger confirmation or confirmation and reconfirmation of the presence of the magnetic field from measurements from one or more of the other Hall sensors.

21 Claims, 7 Drawing Sheets

(56) References Cited

U.S. PATENT DOCUMENTS

| | | |
|---|---|---|
| 8,717,026 B2 | 5/2014 | Shankar et al. |
| 8,750,961 B1 | 6/2014 | Ries et al. |
| 2007/0191914 A1 | 8/2007 | Stessman |
| 2009/0157146 A1 | 6/2009 | Linder et al. |
| 2010/0327887 A1 | 12/2010 | Denison et al. |
| 2011/0106204 A1 | 5/2011 | Yoon et al. |
| 2011/0152674 A1 | 6/2011 | Doerr |
| 2011/0187360 A1 | 8/2011 | Maile et al. |
| 2011/0234218 A1 | 9/2011 | Lagouge |

HALL SENSOR CIRCUIT FOR MAGNETIC FIELD DETECTION IN IMPLANTABLE MEDICAL DEVICE

This application is a U.S. National Stage filing under 35 U.S.C. 371 of International Application No. PCT/US2017/042595, filed Jul. 18, 2017, which claims the benefit of U.S. Provisional Application No. 62/383,259, which was filed on Sep. 2, 2016 and is entitled, "HALL SENSOR CIRCUIT FOR MAGNETIC FIELD DETECTION IN IMPLANTABLE MEDICAL DEVICE," the entire content of which is incorporated herein by reference.

TECHNICAL FIELD

The disclosure relates to implantable medical devices (IMDs) and, more particularly, to magnetic field detection with IMDs.

BACKGROUND

An implantable medical device (IMD) may be exposed to electromagnetic interference (EMI). For example, certain types of medical procedures may need to be performed on a patient within whom the IMD is implanted for purposes of diagnostics or therapy. A patient carrying an implanted IMD may need, for example, to have a magnetic resonance imaging (MRI) scan, a computed tomography (CT) scan, an electrocautery procedure, a diathermy procedure or another type of medical procedure that produces a magnetic field, an electromagnetic field, an electric field or other type of electromagnetic energy. The electromagnetic energy produced by such medical procedures may interfere with the operation of the IMD. For example, the electromagnetic energy may interfere with operation of the internal circuitry of the IMD and/or alter the delivery of therapy by the IMD.

SUMMARY

This disclosure describes example techniques for determining presence of a magnetic field, such as one generated from a magnetic resonance imaging (MRI) field. In some examples, an implantable medical device (IMD) may selectively enter a safe mode based at least in part on the determination.

In one example, a chopper circuit amplifies and demodulates a voltage generated at a first set of terminals of a first Hall sensor due to modulated current applied through an orthogonal second set of terminals of the first Hall sensor. Processor circuitry determines presence of a magnetic field based on the output of the chopper circuit without the chopper circuit applying current through the first set of terminals and amplifying and demodulating voltage generated at the second set of terminals.

The determination of the presence of the magnetic field from the output of the chopper circuit may cause the chopper circuit to repeat the above techniques with respect to a second and/or third Hall sensor to confirm the presence of the magnetic field. In response to determination of the presence of the magnetic field or determination and confirmation of the presence of the magnetic field, the IMD may configure itself in an MRI safe mode.

In one aspect, this disclosure is directed to a method of magnetic field detection, the method comprising modulating, at a frequency, a current applied through first and second terminals of a Hall sensor, amplifying a voltage across third and fourth terminals of the Hall sensor to generate an amplified voltage, wherein the voltage is generated at least in part in response to the current being applied through the first and second terminals of the Hall sensor, demodulating, at the same frequency, the amplified voltage to generate a demodulated signal, determining presence of a magnetic field based on the demodulated signal, wherein the presence of the magnetic field is determined without application of a current through the third and fourth terminals of the Hall sensor and without amplification of a voltage across the first and second terminals, and entering an implantable medical device into a safe mode based in part on the determination of the presence of the magnetic field.

In another aspect, this disclosure is directed to an implantable medical device (IMD) for magnetic field detection, the IMD comprising a Hall sensor, a magnetic field detection circuit configured to modulate, at a frequency, a current applied through first and second terminals of the Hall sensor, amplify a voltage across third and fourth terminals of the Hall sensor to generate an amplified voltage, wherein the voltage is generated at least in part in response to the current being applied through the first and second terminals of the Hall sensor, and demodulate, at the same frequency, the amplified voltage to generate a demodulated signal. The IMD also includes processing circuitry configured to determine presence of a magnetic field based on the demodulated signal, wherein the presence of the magnetic field is determined without application of a current through the third and fourth terminals of the Hall sensor and without amplification of a voltage across the first and second terminals, and enter the IMD into a safe mode based in part on the determination of the presence of the magnetic field.

In another aspect, this disclosure is directed to an implantable medical device (IMD) for magnetic field detection, the IMD comprising means for modulating, at a frequency, a current applied through first and second terminals of a Hall sensor, means for amplifying a voltage across third and fourth terminals of the Hall sensor to generate an amplified voltage, wherein the voltage is generated at least in part in response to the current being applied through the first and second terminals of the Hall sensors, means for demodulating, at the same frequency, the amplified voltage to generate a demodulated signal, means for determining presence of a magnetic field based on the demodulated signal, wherein the presence of the magnetic field is determined without application of a current through the third and fourth terminals of the Hall sensor and without amplification of a voltage across the first and second terminals, and means for entering an implantable medical device into a safe mode based in part on the determination of the presence of the magnetic field.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
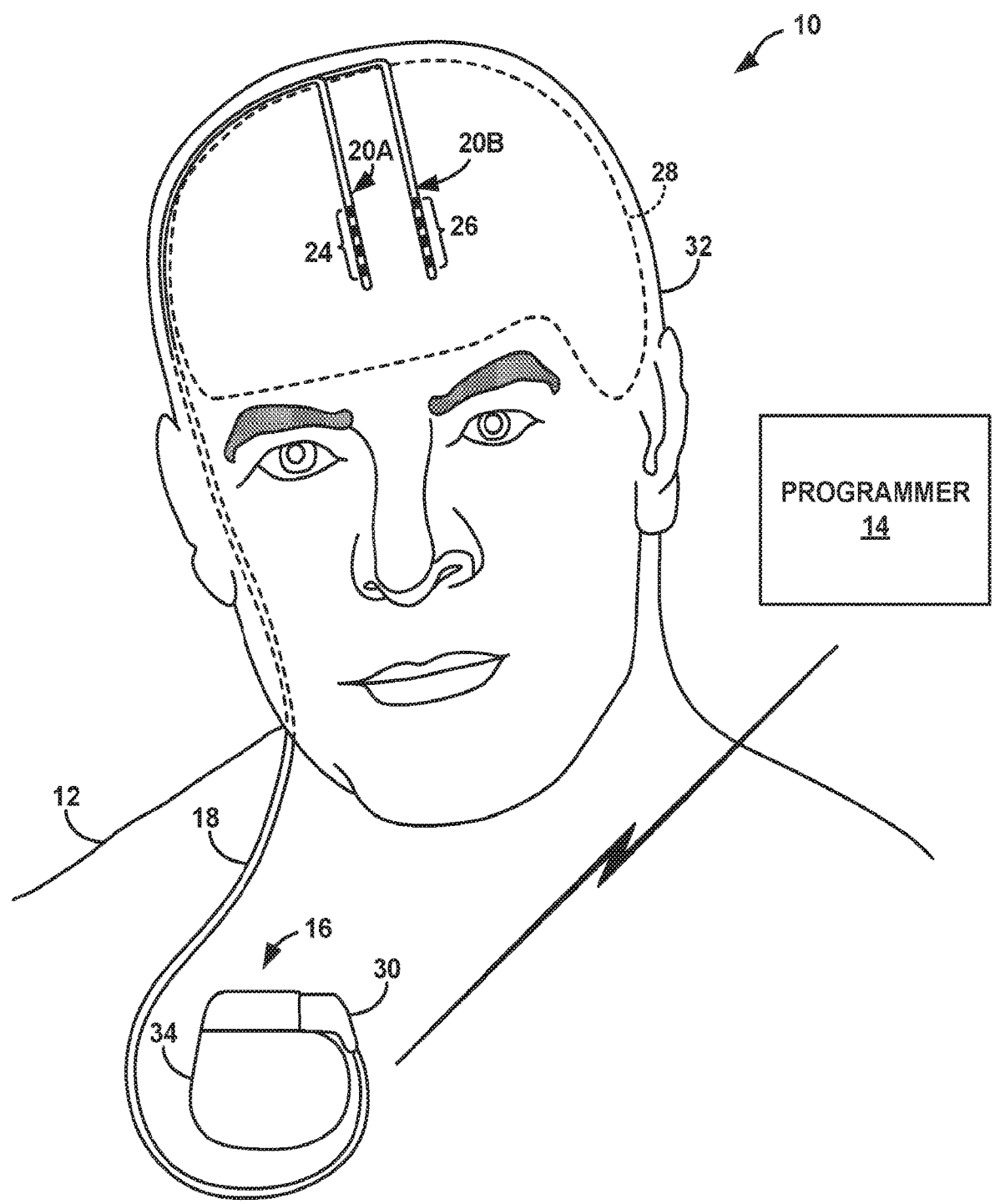
FIG. 1 is a conceptual diagram illustrating an example implantable medical device (IMD), in a therapy system, that is configured to selectively enter a safe mode in response to detection of a magnetic field.

This disclosure describes techniques for an implantable medical device (IMD) to detect a magnetic field of sufficient amplitude to selectively enter a safe mode in response to the detection of a magnetic field of sufficient amplitude and detect that the magnetic field is no longer present, and exit the safe mode in response to determination that the magnetic field is no longer present. In the safe mode, the IMD may adjust operation of the IMD. In some examples, in the safe mode, the IMD may be protected from one or more effects of the magnetic field on the components of the IMD. For example, the magnetic field may affect operation of some aspects of the IMD. The magnetic field may be caused by a magnetic resonance imaging (MM) field, and by adjusting operation of the IMD in the safe mode, the IMD may be protected from, or made more resistant to the effects of the MM field, allowing patients with IMDs to have Mill's or other procedures performed without substantially impacting IMD operation.

A sensor, such as a Hall sensor, generates an electrical potential (voltage) across two terminals in response to a magnetic field, perpendicular to the Hall sensor, applied to the Hall sensor and due to flow of an excitation current through the Hall sensor (e.g., an AC current through the Hall sensor). If the voltage across the terminals is greater or less than a threshold then there is a high probability that there exists a magnetic field around the Hall sensor. For instance, a Hall sensor may be formed as a rectangle, where each side forms a terminal. The excitation current may enter and exit through two opposite terminals, and the voltage is generated across the other two terminals.

In some examples described in this disclosure, a magnetic field detection circuit includes a plurality of Hall sensors configured to detect magnetic fields in different planes such that the magnetic field detection circuit can detect a magnetic field in any of the three dimensions. For example, the magnetic field detection circuit includes a first Hall sensor configured to detect magnetic fields in the X-plane, a second Hall sensor configured to detect magnetic fields in the Y-plane, and a third Hall sensor configured to detect magnetic fields in the Z-plane. The three Hall sensors may be formed together on a common structure or each Hall sensor may be formed in separate structures. Three Hall sensors are described for ease of disclosure, but in general, the techniques described in this disclosure may function with two or more Hall sensors.

One or more chopper-amplifiers may be coupled to respective Hall sensors and output an electrical signal indicative of the voltage on the terminals of respective Hall sensors. In this disclosure, for ease of description only, one chopper-amplifier that selectively couples to different Hall sensors is described; however, in some examples, there may be one chopper-amplifier for each of the Hall sensors, resulting in three chopper-amplifiers, or any combination of one or more chopper-amplifiers.

Detecting magnetic fields using Hall sensors may be impacted by the inherent offset of Hall sensors. Even if there is no magnetic field, a Hall sensor may generate a voltage across terminals in response to the excitation current. The voltage is an offset voltage, and may negatively impact headroom. For instance, the chopper-amplifier amplifies the offset voltage, and if the offset voltage is sufficiently high or the amplifier gain is sufficiently high, the output of the chopper-amplifier may approach the rail voltage (e.g., the maximum voltage that the chopper-amplifier can output), thereby saturating the amplified sensor output. The headroom may be the difference between the rail voltage and the output of the chopper-amplifier. Because the offset voltage may cause the output of the chopper-amplifier to be approximately equal to the rail voltage, a slight amount of magnetic field may cause the output of the chopper-amplifier to equal to the rail voltage.

In this case, the output of the chopper-amplifier may not be usable to determine the amount of magnetic field applied to a Hall sensor because almost any amount of magnetic field causes the output of the chopper-amplifier to be at the rail voltage due to the offset voltage. For example, the output of the chopper-amplifier may be approximately equal to the rail voltage if the magnetic field is at a relatively low level, medium level, or high level because the output of the chopper-amplifier will be the same for all three levels.

Some techniques utilize offset correction techniques to mitigate the effects of the offset voltage. However, offset correction techniques require additional power, which may not be desirable in low power devices or devices where keeping power consumption low to extend battery life is important, such as medical devices.

The example techniques described in this disclosure provide for magnetic field detection without needing to compensate for the inherent Hall sensor voltage offset. The plurality of Hall sensors may be initially driven with an excitation current without the presence of a magnetic field and the output of the chopper-amplifier or the generated voltage of the Hall sensor itself is stored as a baseline measurement. In operation, a circuit coupled to the chopper-amplifier may determine the presence of a magnetic field based detection of shift in the output of the chopper-amplifier relative to the baseline measurement.

To mitigate against the headroom issue, the amplitude of the excitation current may be relatively low. For example, the amplitude of the excitation current may be approximately 10 microamps to 100 microamps rather than 1 mA. With such low amplitude excitation currents, the voltage generated by Hall sensor in response to a magnetic field may be relative low. Even with the offset voltage, the amplitude of the output of the chopper-amplifier may not approach the rail voltage because the generated voltage across the Hall sensor is relatively low. By keeping the amplitude of the excitation current low, the circuit may be able to determine the magnetic field level based on a comparison with the baseline measurement.

While utilizing a Hall sensor and a chopper-amplifier to detect the presence of a magnetic field may be relatively effective, due to the low noise and reduced headroom, there may be possibility of false detection of a magnetic field or false determination that the magnetic field is no longer present. In examples described in this disclosure, the output of a first Hall sensor may be used to preliminarily detect the presence of a magnetic field, and at least a second Hall sensor may be use to confirm the existence of the magnetic field.

Also, the first Hall sensor may not detect magnetic fields from all angles. For instance, if the patient is oriented in a particular way relative to the magnetic field, the first Hall sensor may not detect this magnetic field. Accordingly, having a second Hall sensor, and possibly a third Hall sensor, each in different planes relative to one another may ensure that a magnetic field is detected regardless of its angle.

As an example, the Z-plane Hall sensor may be a relatively sensitive sensor. If the circuit determines that output of the chopper-amplifier, when coupled to the Z-plane Hall sensor, indicates that a magnetic field is present, the circuit may determine the output of the chopper-amplifier, when coupled to at least one of the X-plane Hall sensor and Y-plane Hall sensor. If the circuit determines based on one or both outputs of the X- and Y-plane Hall sensors, that a magnetic field is present (e.g., confirming the detection by the Z-plane Hall sensor), the circuit may cause the IMD to enter a safe mode. Once the IMD enters the safe mode, the circuit may rely on the outputs of the chopper-amplifier when the voltages generated by two or more of the Hall sensors indicates that the magnetic field is no longer present.

In the above example, the circuit may periodically poll the Z-plane Hall sensor (e.g., periodically output the excitation current through the Z-plane Hall sensor and determine the output of the chopper-circuit coupled to the Z-plane Hall sensor). If the output of the chopper-circuit indicates presence of the magnetic field, the circuit may poll the X-plane and/or Y-plane Hall sensors to confirm the presence of the magnetic field. In this manner, the example techniques allow for low power and accurate detection of a magnetic field to selectively cause an IMD to enter safe mode in response to the presence of a magnetic field and exit safe mode in response to the magnetic field no longer being present.

FIG. 1 is a conceptual diagram illustrating an example implantable medical device (IMD) 16, in a therapy system 10, that is configured to selectively enter safe mode in response to detection of a magnetic field. In some examples, therapy system 10 may deliver therapy to patient 12 to address various patient conditions. Patient 12 ordinarily will be a human patient. In some cases, however, therapy system 10 may be applied to other mammalian or non-mammalian non-human patients.

One example of patient conditions addressed by IMD 16 is a movement disorder. A movement disorder may be characterized by one or more symptoms, such as, but not limited to, impaired muscle control, motion impairment or other movement problems, such as rigidity, bradykinesia, rhythmic hyperkinesia, non-rhythmic hyperkinesia, dystonia, tremor, and akinesia. In some cases, the movement disorder may be a symptom of Parkinson's disease or Huntington's disease. However, the movement disorder may be attributable to other patient conditions.

As other examples, IMD 16 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD).

Treatment of other patient disorders via delivery of therapy to brain 28 or another suitable target therapy delivery site in patient 12 are also contemplated. In some examples, IMD 16 may deliver stimulation to a spinal cord of patient 12 to provide pain therapy, as an example.

Although FIG. 1 illustrates examples where IMD 16 is a neurostimulator, the techniques are not limited. In some examples, IMD 16 may provide cardiac stimulation therapy (e.g., IMD 16 is a pacemaker and/or cadioverter-defibrillator) to address conditions such as cardiac arrhythmia, cardiac fibrillation, and the like. As additional examples, IMD 16 may provide pelvic floor stimulation therapies for symptoms or conditions such as pain, urinary or fecal incontinence, sexual dysfunction, gastric stimulation (e.g., for obesity), or gastroparesis, peripheral nerve stimulation for pain or other symptoms, and may provide information useful in controlling electrical stimulation or drug delivery to a variety of tissue sites, such as the heart, the brain, the spinal cord, pelvic nerves, peripheral nerves, or the gastrointestinal tract of a patient. Hence, techniques described in this disclosure for detecting magnetic fields may be applied to any of a variety of IMDs, including stimulation devices, drug delivery devices, and other devices. Furthermore, although this disclosure is described with examples of IMD 16, the techniques described in this disclosure may be applicable to examples of an external medical device.

As described in more detail, this disclosure describes a magnetic field detection circuit. The circuit may be part of IMD 16, part of a separate IMD, or part of an external medical device. In general, the magnetic field detection circuit as described in this disclosure may be integrated with, housed in, coupled to, or otherwise associated with an external or implantable medical device, such as a cardioverter/defibrillator, spinal cord stimulator, pelvic nerve stimulator, deep brain stimulator, gastrointestinal stimulator, peripheral nerve stimulator, or muscle stimulator, and also may be used in conjunction with implantable or external drug delivery devices. For example, the magnetic field detection circuit may reside within an implantable medical device housing or a lead or catheter coupled to such a device.

The magnetic field detection circuit may be used in conjunction with different therapeutic applications, such as cardiac stimulation, deep brain stimulation (DBS), spinal cord stimulation (SCS), pelvic stimulation for pelvic pain, incontinence, or sexual dysfunction, gastric stimulation for gastroparesis, obesity or other disorders, or peripheral nerve stimulation for pain management. Stimulation also may be used for muscle stimulation (e.g., functional electrical stimulation (FES)) to promote muscle movement or prevent atrophy.

For ease of understanding, the following describes the example where IMD 16 provides deep brain stimulation (DBS), as one example, as illustrated in FIG. 1. In the example shown in FIG. 1, therapy system 10 includes medical device programmer 14, IMD 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a DBS system because IMD 16 provides electrical stimulation therapy directly to tissue within brain 28 (e.g., a tissue site under the dura mater of brain 28 or one or more branches or nodes, or a confluence of fiber tracks). In other examples, leads 20 may be positioned to deliver therapy to a surface of brain 28 (e.g., the cortical surface of brain 28). In some examples, IMD 16 may provide cortical stimulation therapy to patient 12 (e.g., by delivering electrical stimulation to one or more tissue sites in the cortex of brain 28). In some examples, IMD 16 may provide vagal nerve stimulation (VNS) therapy to patient 12 by delivering electrical stimulation to one or more vagal nerve tissue sites.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as (e.g., the anterior thalamic nucleus, the internal capsule, the cingulate, the fornix, the mammillary bodies, the mammillothalamic tract (mammillothalamic fasciculus), and/or hippocampus). For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry, may include an array of electrodes positioned at different axial positions along the length of a lead, as well as at different angular positions about the periphery (e.g., circumference) of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage), pulse amplitude, pulse width, a waveform shape, etc. In addition, if different electrodes are available for delivery of stimulation, a therapy parameter of a therapy program may be further characterized by an electrode combination, which may define selected electrodes and their respective polarities.

In some examples, IMD 16 may include a sensing module that is configured to sense bioelectrical signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical signals via one or more of the electrodes 24, 26 that are also used to deliver electrical stimulation to brain 28. In other examples, one or more of electrodes 24, 26 may be used to sense bioelectrical signals while one or more different electrodes 24, 26 may be used to deliver electrical stimulation.

Depending on the particular stimulation electrodes and sense electrodes used by IMD 16, IMD 16 may monitor bioelectrical signals and deliver electrical stimulation at the same region of brain 28 or at different regions of brain 28. In some examples, the electrodes used to sense bioelectrical signals may be located on the same lead used to deliver electrical stimulation, while in other examples, the electrodes used to sense bioelectrical signals may be located on a different lead than the electrodes used to deliver electrical stimulation. In some examples, a bioelectrical signal of patient 12 may be monitored with external electrodes (e.g., scalp electrodes). Moreover, in some examples, the sensing module that senses bioelectrical signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a local field potential (LFP) sensed from within one or more regions of a patient's brain, and/or action potentials from single cells within the patient's brain. In some examples, LFP data can be measured ipsilaterally or contralaterally and considered as an average (e.g., a maximum or minimum or a heuristic combination thereof) or as some other value. The location at which the sensed signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function (i.e., a power button), the buttons and the keypad may be soft keys that change in function depending upon the section of the user interface currently viewed by the user, or any combination thereof. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), the Internet, or a cellular telephone network, for example.

System 10 shown in FIG. 1 is merely one example of a therapy system that is configured to perform the techniques described in this disclosure. Systems with other configurations of leads, electrodes, and sensors are possible. For example, in other implementations, IMD 16 may be coupled to additional leads or lead segments having one or more electrodes positioned at different target tissue sites, which may be within brain 28 or outside of brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimulator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to deliver electrical stimulation therapy to brain of patient 12, but, rather, is only configured to sense one or more physiological parameters of patient 12, including a bioelectrical brain signal of patient 12. This type of IMD 16 may a patient monitoring device useful for diagnosing patient 12, monitoring a patient condition 12, or to train IMD 16 or another IMD for therapy delivery.

Patient 12, implanted with IMD 16, may receive certain therapy or diagnostic procedures, such as a magnetic resonance imaging (MM) scan. An MM uses high frequency radio frequency (RF) pulses, a static magnetic field, and gradient magnetic fields to create image data regarding patient 12. An MM may have a frequency of approximately 42 MHz per tesla. One example MM system uses 1.5 tesla magnetic fields and has a corresponding RF frequency of approximately 64 MHz.

The techniques described in this disclosure are not limited to any specific MM systems, and other MM systems are contemplated by this disclosure. The techniques described in this disclosure should not be considered limited to MM systems, and may be extendable more generally to detection of a magnetic field, whether or not the magnetic field is due to an MM scan. For ease of description, this disclosure is described with respect to an MRI scan.

The gradient magnetic fields and RF pulses of the MRI scan may induce currents within IMD 16, lead extension 18, and/or leads 20. The induced current may affect operation of some of the circuitry within IMD 16, as well as cause other possible unwanted effects. Because MRI scans or magnetic fields more generally may cause unwanted effects, IMD 16 may be configured to detect the presence of a magnetic field so that corrective actions can be taken. According to techniques described in this disclosure, IMD 16 may include a magnetic field detection circuit configured to detect the existence of a magnetic field. In response to detection of the magnetic field, IMD 16 may be configured in an MRI safe mode to protect the circuitry of IMD 16, as well as mitigate against other effects.

One example way to detect existence of a magnetic field is with a Hall sensor. A Hall sensor may be rectangular in shape, although a rectangular shape is not a requirement, and includes four terminals. As an example, this disclosure utilizes three Hall sensors. In some examples, one of the Hall sensors may be square, and the other two Hall sensors are rectangles, or two of the Hall sensors are squares, and one of the Hall sensors is square. All three Hall sensors may be square or all three Hall sensors may be rectangles. Other shapes and combinations are also possible.

Two of the terminals of the Hall sensor are used to cause an excitation current to flow through the Hall sensor. If a magnetic field, perpendicular to the Hall sensor, is present through the Hall sensor, the magnetic field causes a voltage to be generated across the other two terminals. The resulting voltage across the two terminals is proportional to the magnetic field level. The resulting voltage across the two terminals of the Hall sensor has a relatively low amplitude and an amplifier may be used to amplify the voltage.

Each instance that the excitation current flows through the Hall sensor to determine the existence of a magnetic field causes IMD 16 to expend power. Because regular testing for the existence of a magnetic field is advisable for IMD 16, the techniques described in this disclosure provide a way to expend reduced power for magnetic field detection.

To minimize the power, the amplitude of the excitation current may be relatively low. One possible result of using a low amplitude excitation current is that the amplitude of the resulting voltage is relatively low. Accordingly, an instrumentation amplifier is coupled to the Hall sensor to amplify the voltage.

An instrumentation amplifier described in this disclosure may be configured for very low power applications. IMD 16, for example, may be characterized by finite power resources that are required to last several months or years. Accordingly, to promote device longevity, sensing and therapy circuits of IMD 16 are generally designed to consume very small levels of power. As an example, operation of a magnetic field detection circuit incorporating the Hall sensor and an instrumentation amplifier, as described in this disclosure, may require a supply current of less than 2.0 microamps. In some examples, such a magnetic field detection circuit may consume supply current in a range of approximately 100 nanoamps to 1.0 microamps. The Hall sensor operates with excitation currents, and the supply current of 2.0 microamps or 100 nanoamps to 1.0 microamps excludes the excitation current. In some examples, the excitation current may be approximately 10 microamps, but the excitation current is not delivered at all times (e.g., the excitation current is delivered for a short amount of time over a duration). Accordingly, on average, the excitation current does not add much to the overall operational current.

Although medical devices are described for purposes of illustration, a magnetic field detection circuit may be used in a variety of medical and non-medical test and measurement applications. In each case, a magnetic field detection circuit may be configured to draw very low power, yet provide precise and accurate measurement.

Low power devices, such as the instrumentation amplifier, may be susceptible to aliasing, DC offsets within the amplifier, and to noise such as 1/f noise. In the examples described in this disclosure, the instrumentation amplifier may be a chopper-amplifier, which is a low power amplifier but less susceptible to aliasing, internal DC offsets, and noise. A chopper-amplifier includes a modulator, amplifier, and demodulator. The modulator modulates an input signal (e.g., the current across the Hall sensor) at a chopper frequency prior to amplification, the amplifier of the chopper-amplifier amplifies the modulated input signal, and the demodulator demodulates the amplified signal. A low-pass filter or integrator filters the output of the amplifier such that the amplified signal is back at the baseband (e.g., measurement band). This process confines the noise and offset generated by the amplifier to the chopper frequency band, thereby preventing it from entering the measurement band.

Using the chopper-amplifier allows for amplification of low voltage signals generated from low excitation current levels (e.g., microampsrange). Applying low excitation current levels to the Hall sensor and generating low voltage signals across the Hall sensor may allow for detecting a magnetic field without needing offset voltage correction, although applying offset correction is possible.

There may be some inherent voltage offset in Hall sensor outputs. Even if there is no magnetic field, applying an excitation current to a Hall sensor causes a voltage to generate across the Hall sensor. This voltage is referred to as a Hall sensor DC offset. This Hall sensor DC offset should not be confused with the DC offset described above for the chopper-amplifier. The DC offset described above for the chopper-amplifier is the DC offset within the chopper-amplifier itself. The Hall sensor DC offset refers to the offset added to any actual voltage generated due to magnetic field.

During manufacturing of the Hall sensor or IMD 16, a technician may determine the Hall sensor DC offset, which may form a baseline measurement. The actual voltage caused by the magnetic field may be the measured voltage plus/minus the baseline measurement. For example, assume that the amplified voltage generated across the Hall sensor is 486 millivolts in response to presence of a 100 gauss magnetic field, and assume that the Hall sensor DC offset is 481 millivolts. In this example, the voltage indicative of the magnetic field level is 486 millivolts minus 481 millivolts.

As another example, assume that the amplified voltage generated across the Hall sensor is 476 millivolts in response to presence of a 100 gauss magnetic field, but in an opposite direction than the 100 gauss magnetic field of the previous example. Keeping with the Hall sensor DC offset being 481 millivolts, the voltage indicative of the magnetic field level is 481 millivolts minus 476 millivolts. In general, the voltage indicative of the magnetic field may be the absolute value of (baseline DC offset of the Hall sensor minus amplified voltage generated across the Hall sensor), or the absolute value of (amplified voltage generated across the Hall sensor minus baseline DC offset of the Hall sensor).

In the above example, during manufacturing, such as production level, the technician, some automated computerized system, or a combination may define certain calibration values for IMD 16. At that point, the technician may determine the baseline measurement for the Hall sensors.

When there is a magnetic field, based on magnetic field and IMD 16 location, the voltage that the Hall sensors output could shift positive or negative. A plus magnetic field exists if on the positive side of magnetic field, but if change the polarity of the magnetic field, then shift is negative.

In some examples, in addition to the Hall sensors, there may be additional causes for offset. The baseline measurement may include all sources of offsets. As described in more detail, the measurements from the Hall sensors and amplifiers is converted to a digital value (e.g., during manufacturing with no magnetic field present, the excitation current outputs across the Hall sensor, and digital value is measured). This digital value is the baseline measurement against which the actual measurement is compared. For instance, a comparison between the digital value of the baseline measurement and the digital value of the actual value may be a shift in 50 least significant bits (LSBs), and may be used to determine whether the shift is large enough to indicate presence of the magnetic field.

Shift in LSBs refers to a difference in the values between the baseline measurement and the actual measurement. For example, the digital value of the baseline measurement can be converted to a first base 10 value, and the digital value of the actual measurement can be converted to a second base 10 value. The shift in the LSBs refers to the difference between the first and second base 10 values. For instance, the absolute value of the difference between the first and second base 10 values may be 50.

In this example, if the absolute value of the difference between the baseline measurement and the actual measurement is greater than a threshold, then IMD 16 may determine that a magnetic field is present. If the absolute value of the difference between the baseline measurement and the actual measurement is less than or equal to the threshold, then IMD 16 may determine that a magnetic field is not present.

One effect of the Hall sensor DC offset is reducing headroom of the chopper-amplifier. There may be a maximum output voltage level of the chopper-amplifier, referred to as the rail voltage. The headroom of the chopper-amplifier refers to the difference between the rail voltage and the voltage that the chopper-amplifier outputs when the input is the Hall sensor DC offset.

The amount of headroom of the chopper-amplifier is one factor that sets the range of magnetic field levels that can be detected. IMD 16 may be able to resolve the magnetic field levels for all magnetic fields that do not cause the chopper-amplifier to output the rail voltage and may not be able to resolve the magnetic field levels for any magnetic field greater than the magnetic field level that causes the chopper-amplifier to output the rail voltage.

For example, assume that the headroom is 200 mV and that a magnetic field having a threshold magnetic field level causes the Hall sensor to output a voltage equal to 200 mV plus Hall sensor DC offset. In this example, for a magnetic field with a magnetic field level below the threshold magnetic field level, IMD 16 may be able to determine the actual magnetic field level. For all magnetic fields with magnetic field levels greater than the threshold magnetic field level, IMD 16 may not be able to determine the actual magnetic field level because the output of the chopper-amplifier will be at the rail voltage. For instance, if a first magnetic field level and a second magnetic field level both cause the chopper-amplifier to output the rail voltage, then IMD 16 may not be able to accurately determine whether the magnetic field is as the first magnetic field level or the second magnetic field level.

In the example techniques described in this disclosure, because the excitation current is relatively low (e.g., 10 to 100 microamps instead of 1 mA), the voltage generated across the Hall sensor is relatively low. Because the voltage generated across the Hall sensor is relatively low, there is a relatively large range of magnetic field levels that IMD 16 can resolve. For example, assume that for every increase of 100 gauss in the magnetic field level, the voltage generated across the Hall sensor increases by 1 mV. If the headroom is 20 mV, then the range of magnetic field levels that IMD 16 can resolve is approximately 2000 gauss. If, on the other hand, the voltage generated across the Hall sensor increases by 10 mV for every increase of 100 gauss, such as in examples where a higher excitation current is used, then the range of magnetic field levels that IMD 16 can resolve is approximately 200 gauss.

In the example techniques described in this disclosure, during manufacturing or after implantation, IMD 16 may execute a calibration process. In the calibration process, patient 12 may not be in a magnetic field. IMD 16 may apply the excitation current which causes the Hall sensor to generate the Hall sensor DC offset. The chopper-amplifier receives and amplifies the Hall sensor DC offset. IMD 16 may store the resulting output from the chopper-amplifier as a baseline measurement. Then, during operation, if the chopper-amplifier outputs a voltage that is greater than or less than the baseline measurement by a certain threshold, IMD 16 may detect the presence of a magnetic field. For example, if the absolute value of the difference between the voltage that the chopper-amplifier outputs and the baseline measurement is greater than a threshold, IMD 16 may detect the presence of a magnetic field.

Accordingly, IMD 16 may be configured to detect the presence of the magnetic field without needing to compensate for the Hall sensor DC offset by keeping the generated voltage across the Hall sensor relatively low using low level excitation currents. Some other techniques attempt to compensate for the Hall sensor DC offset to increase the headroom. However, such techniques may require additional power as compared to the example techniques described in this disclosure.

As one example, to compensate for the Hall sensor DC offset, a device outputs an excitation current (possibly in the mA range such 1 mA) through a first and second terminal of the Hall sensor and amplifies the voltage across a third and fourth terminal of the Hall sensor. Then, the device outputs an excitation current through the third and fourth terminals of the Hall sensor and amplifies the voltage across the third and fourth terminals. Based on these two amplified voltages, the devices forms a feedback path to cancel the effects of the Hall sensor DC offset.

However, such techniques require twice the excitation current (e.g., once through the first and second terminals, and once through the third and fourth terminals) and twice the amplification (e.g., once for the voltage across the third and fourth terminals, and once for the voltage across the first and second terminals). In the example techniques described in this disclosure, IMD 16 may be configured to determine the presence of a magnetic field based on applying an excitation current through the first and second terminals of the Hall sensor and amplifying the voltage across the third and fourth terminals of the Hall sensor without application of a current through the third and fourth terminals of the Hall sensor and without amplification of a voltage across the first and second terminals of the Hall sensor. In this manner, IMD 16 may determine the presence of the magnetic field while expending reduced power for magnetic field detection.

Furthermore, in some examples, rather than using only one Hall sensor to determine the presence of the magnetic field, IMD 16 may utilize a plurality of Hall sensors to determine the presence of the magnetic field. In such examples, the output of a chopper-amplifier coupled to one of the Hall sensors may indicate presence of the magnetic field, and the output of the chopper-amplifier coupled to the one or more of the other Hall sensors may confirm the presence of the magnetic field.

The plurality of Hall sensors may include a Z-plane Hall sensor, an Y-plane Hall sensor, and a X-plane Hall sensor. The Z-plane Hall sensor may be oriented substantially in the dorsal-ventral plane of patient 12. The Y-plane Hall sensor may be oriented substantially in the superior-inferior plane of patient 12. The X-plane Hall sensor may be oriented substantially in the medial-lateral plane of patient 12.

In example techniques described in this disclosure, IMD 16 may apply the excitation current across a first Hall sensor (e.g., Z-plane Hall sensor) and based on the amplified voltage across the first Hall sensor, IMD 16 may determine whether a magnetic field is present or not present. If IMD 16 determines that the magnetic field is present based on the measurement from the first Hall sensor, IMD 16 may apply the excitation current across the second Hall sensor (e.g., Y-plane Hall sensor or X-plane Hall sensor) and based on the amplified voltage across the second Hall sensor, IMD 16 may confirm the presence of the magnetic field. IMD 16 may repeat these steps with the third Hall sensor (e.g., the other one of the Y-plane Hall sensor or the X-plane Hall sensor).

In such examples, if all three measurements indicate that a magnetic field is present, IMD 16 may configure itself into a safe mode. In some examples, rather than relying on all three measurements to indicate that a magnetic field is present, IMD 16 may rely on two of three measurements.

Although the above example describes the order of measurement as Z-plane Hall sensor, then Y-plane Hall sensor, and then X-plane Hall sensor, the example techniques described in this disclosure are not so limited. In some examples, any order of the measurements from the Hall sensors may be possible for determining and confirming the presence of a magnetic field. Because when patient 12 is approaching towards an MRI system (e.g., walking towards the MM machine), the Z-plane Hall sensor may most directly receive the magnetic field, the examples described in this disclosure are described with first determining the presence of a magnetic field with the Z-plane Hall sensor and then confirming with one or more of the Y-plane and X-plane Hall sensors. However, more generally, the example techniques may utilize measurements from a first Hall sensor (e.g., one of Z-, Y-, or X-plane Hall sensor) for determining presence of a magnetic field and utilize measurements from the second and/or third Hall sensor (e.g., other ones of Z-, Y-, or X-plane Hall sensors) for confirming presence of the magnetic field.

In some examples, which sensor is the first, second, and third Hall sensor may change. For example, if IMD 16 determines that patient 12 is prone (e.g., via an accelerometer), then the first Hall sensor may be the Y-plane Hall sensor, and if IMD 16 determines that patient 12 is upright (e.g., via the accelerometer), then the first Hall sensor may be the Z-plane Hall sensor. Other cases for changing the order in which IMD 16 measures the Hall sensors may be possible and contemplated by the example techniques described in this disclosure.

To ensure that IMD 16 detects the presence of a magnetic field, IMD 16 may periodically poll measurements from the first Hall sensor. For example, IMD 16 may apply an excitation current through the first Hall sensor periodically (e.g., every 10 seconds), and determine whether the output of the chopper-amplifier is greater than or less than a threshold (e.g., a change in the output of the chopper-amplifier is greater than a threshold). If IMD 16 determines that the output of the chopper-amplifier is greater than or less than the threshold (e.g., a change in the output of the chopper-amplifier is greater than a threshold), IMD 16 may repeat these steps with one or more both of the second and third Hall sensors. If IMD 16 determines that the output of the chopper-amplifier is less than or equal to the threshold (e.g., a change in the output of the chopper-amplifier is less than or equal to a threshold), IMD 16 may wait and check for the presence of a magnetic field after a period of time (e.g., 10 seconds).

The first Hall sensor may be configured with high sensitivity and/or a low threshold for determining the presence of the magnetic field with the first Hall sensor may be low. For example, even a slight magnetic field may generate a voltage across the first Hall sensor or even a slight output level from the chopper-amplifier when the chopper-amplifier is coupled to the first Hall sensor may cause IMD 16 to determine that a magnetic field is present. To avoid false detection of a magnetic field, IMD 16 may then utilize the other Hall sensor(s). The second and third Hall sensors may not be configured for low sensitivity and/or high threshold for confirming the presence of the magnetic field with the second and third Hall sensors may be higher than that for the first Hall sensor.

The Hall sensors include an inherent sensitivity. For higher output, a higher excitation or higher magnetic field may be needed. By using a higher excitation current for the second and the third Hall sensor, results in a higher output.

In some examples, for the first Hall sensor, the threshold may be approximately 20 to 50 gauss and a highly sensitive Hall sensor. The second and third Hall sensor may be have lower sensitivity and have a threshold of approximately 500 gauss.

In the event that IMD 16 determines or confirms the presence of a magnetic field, IMD 16 may enter a safe mode. In the safe mode, IMD 16 may disconnect circuitry within IMD 16 from one or more of electrodes 24, 26. This way, electrodes 24, 26 may not be able to conduct any current generated from the magnetic field back to the circuitry within IMD 16. In the safe mode, IMD 16 may also pause or limit delivery of therapy to avoid interference from the magnetic field. In some examples, in addition to disconnecting one or more of electrodes 24, 26 from circuitry within IMD 16, IMD 16 may couple the disconnected electrodes 24, 26 to ground to avoid electrodes 24, 26 from building charge. There may be other ways in which IMD 16 may configure itself in safe mode and the above are merely a few examples for safe mode configuration. In some examples, in safe mode, IMD 16 may perform active recharge across the electrodes and continue to provide therapy that way.

Once in safe mode, IMD 16 may still periodically poll measurements from one or more of the Hall sensors, possibly at smaller period then the polling period for determining the presence of a magnetic field. IMD 16 may remain in safe mode until the measurements from two or more of Hall sensors indicates that there is no magnetic field and return to normal mode (e.g., where IMD 16 can safely deliver therapy) if the measurements from two or more Hall sensors indicates that there is no magnetic field. In this example, IMD 16 may first poll one or both of the less sensitive Hall sensors (e.g., one or more both of the second and third Hall sensors). If the measurements from one or both of second and third Hall sensors indicates that there is no magnetic field, processor circuitry of IMD 16 may poll the sensitive Hall sensor (e.g., first Hall sensor) to confirm that there is no magnetic field.

In this manner, IMD 16 may be configured to selectively enter and exit the safe mode based on the determination that a magnetic field is present or that the magnetic field is no longer present. The techniques to determine the presence of the magnetic field or determine that there is no magnetic field may include determining the presence of the magnetic field from respective voltages generated on two or more Hall sensors. To determine whether the voltages generated on two or more Hall sensors is sufficiently high to indicate presence of a magnetic field, IMD 16 may apply excitation current across a first pair of terminals of the respective Hall sensors and amplify the voltage across a second pair of terminals of the respective Hall sensors without applying excitation current to the second pair terminals of the respective Hall sensors or amplifying voltages across the first pair of terminals of the respective Hall sensors. The amplitude of the excitation current may be relatively low (e.g., 10 microamps to 100 microamps.

Figure 2:
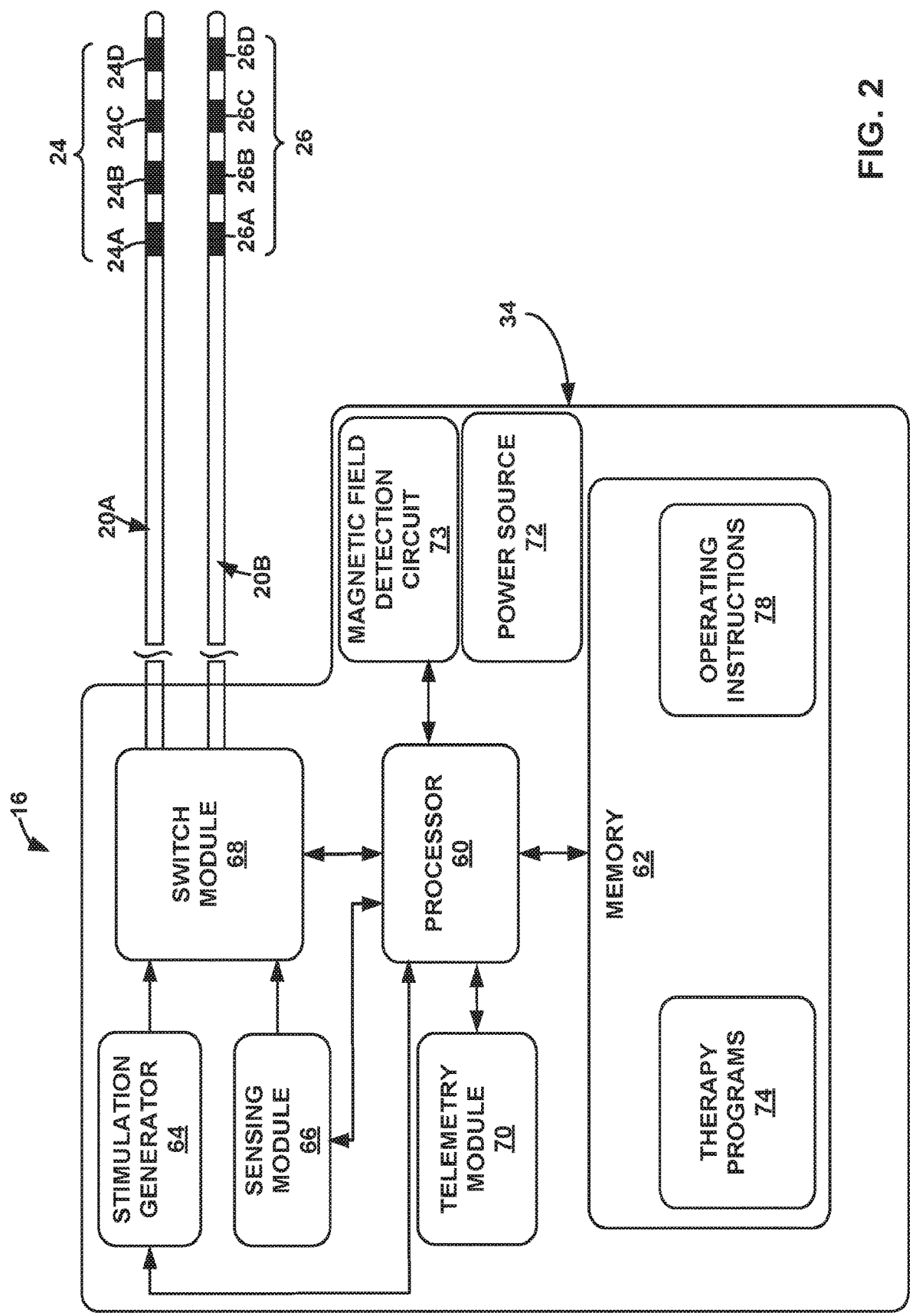
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, power source 72, and magnetic field detection circuit 73. As described in more detail, magnetic field detection circuit 73 may output a digital value that processor 60 receives and uses to determine whether a magnetic field is present or no longer present.

Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74 and operating instructions 78 (e.g., in separate memories within memory 62 or separate areas within memory 62). Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal.

In some examples, memory 62 may also store brain signal data generated by sensing module 66 based on signals received via at least one of electrodes 24, 26 and, in some cases, at least a portion of outer housing 34 of IMD 16, an electrode on outer housing 34 of IMD 16 or another reference electrode. In addition, in some examples, processor 60 may append a time and date stamp to the brain signal data in memory 62. Operating instructions 78 guide general operation of IMD 16 under control of processor 60, and may include instructions for monitoring brains signals within one or more brain regions via electrodes 24, 26 and delivering electrical stimulation therapy to patient 12. Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processing circuitry described in this disclosure, including processor 60, may include any of a variety of fixed function and/or programmable circuitry such as one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 may be configured to control stimulation generator 64 according to therapy programs 74 stored by memory 62 to apply particular stimulation parameter values specified by one or more programs.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Switch module 68 is illustrated as merely one example. In some examples, IMD 16 may not include switch module 68. Rather, IMD 16 may include a plurality of stimulation sources such as current sources that sink or source current and/or a voltage sources that output a positive or a negative voltage. In such examples, each one of electrodes 24, 26 may be coupled to separate ones of the stimulation sources. In some examples, some of electrodes 24, 26 may be coupled to the same stimulation source, and others to another stimulation source, with the possibility that one stimulation source couples to a plurality of electrodes 24, 26. In examples where IMD 16 does not include switch module 68, processor 60 and/or stimulation generator 64 may selectively enable stimulation sources to deliver the stimulation. In some examples, in addition to including a plurality of stimulation sources for one or more electrodes 24, 26, IMD 16 may include switch module 68.

Stimulation generator 64 may be a single channel or multi-channel stimulation generator. In particular, stimulation generator 64 may be capable of delivering, a single stimulation pulse, multiple stimulation pulses or continuous signal including a plurality of frequency components at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). Processor 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker). Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

In accordance with the example techniques described in this disclosure, magnetic field detection circuit 73 is configured to output information that processor 60 uses to determine the presence of a magnetic field. Although magnetic field detection circuit 73 is illustrated as being external to processor 60, one or more components of magnetic field detection circuit 73 may be part of processor 60. For ease of description only, magnetic field detection circuit 73 is described as being external to processor 60.

Magnetic field detection circuit 73 may include an excitation current source, a plurality of Hall sensors (e.g., Z-plane, Y-plane, and X-plane Hall sensors), a chopper-amplifier, an optional analog-to-digital (ADC) converter, and a clock source for controlling the modulation and demodulation of the chopper-amplifier. Tissue impedance measurement circuits and some circuitry within telemetry module 70 may also use similar components such as those of magnetic field detection circuit 73. Accordingly, in some examples, the components of magnetic field detection circuit 73 may also be used for tissue impedance measurement or other functions. As an example, when IMD 16 is to perform tissue impedance measurement, processor 60 may leverage components of magnetic field detection circuit 73 such as the excitation current source, the chopper-amplifier, and clock source for tissue impedance measurement, and then use these components for magnetic field detection when desired. For ease of description, magnetic field detection circuit 73 is described as its own separate circuitry.

During manufacturing or post-implant when there is no magnetic field present, processor 60 may output an instruction to magnetic field detection circuit 73 to cause magnetic field detection circuit 73 to output the voltage from the chopper-amplifier when the Z-plane Hall sensor is coupled to the chopper-amplifier, when the Y-plane Hall sensor is coupled to the chopper-amplifier, and when the X-plane Hall sensor is coupled to the chopper-amplifier. In the examples where magnetic field detection circuit 73 includes the ADC, processor 60 receives the digital value representing the voltage outputted by the chopper-amplifier. In examples where magnetic field detection circuit 73 does not include the ADC, processor 60 may include an ADC to convert the output of the chopper-amplifier to a digital value or may operate using the analog value of the voltage outputted by the chopper-amplifier. The following is described with the example where magnetic field detection circuit 73 includes the ADC, but the techniques function similarly in the example where magnetic field detection circuit 73 does not include the ADC.

Processor 60 receives the digital values from magnetic field detection circuit 73 for when each of the Z-plane, Y-plane, and X-plane Hall sensors are coupled to the chopper-amplifier and when there is no magnetic field. These values represent the respective Hall sensor DC offsets for the Z-plane, Y-plane, and X-plane Hall sensors. Processor 60 stores the Hall sensor DC offsets as baseline measurements for respective Z-plane, Y-plane, and X-plane Hall sensors in memory 62.

Processor 60 may periodically cause magnetic field detection circuit 73 to couple a first Hall sensor (e.g., Z-plane Hall sensor) to the chopper-amplifier circuit and output the digital value. In some examples, processor 60 may compare the received digital value for the first Hall sensor with a baseline measurement for the first Hall sensor. If the shift in the digital value (e.g., could be positive or negative) is greater than a first threshold, processor 60 may determine that a magnetic field is present.

For example, the difference between the received digital value for the Hall sensor and the baseline measurement for the first Hall sensor may be a positive value or a negative value based on the polarity of the magnetic field. Accordingly, if the received digital value for the Hall sensor drops below a threshold because the magnetic field is in a first polarity, then processor 60 may determine that a magnetic field is present. If the received digital value for the Hall sensor goes above a threshold because the magnetic field is in a second polarity, then processor 60 may determine that a magnetic field is present. Stated another way, if the absolute value of the difference between the received digital value for the Hall sensor and the baseline measurement is greater than a threshold, then processor 60 may determine that a magnetic field is present, and if the absolute value of the difference between the received digital value for the Hall sensor and the baseline measurement is less than or equal to the threshold, then processor 60 may determine that a magnetic field is not present.

Processor 60 may use the determination that the magnetic field is present based on the measurement from the first Hall sensor as a factor in causing IMD 16 to enter a safe mode of operation. In some examples, prior to causing IMD 16 to enter a safe mode of operation, processor 60 may confirm the presence of the magnetic field.

For example, in response to a determination that the magnetic field is present based on the measurement from the first Hall sensor, processor 60 may instruct magnetic field detection circuit 73 to couple a second Hall sensor to the chopper-amplifier and receive the digital value for the second Hall sensor. Processor 60 may compare the received digital value for the second Hall sensor with a baseline measurement for the second Hall sensor. If the absolute value of the difference is greater than a second threshold (different than or same as the first threshold), processor 60 may initially confirm that a magnetic field is present. Using confirmation of the magnetic field from the measurement with the second Hall sensor may be sufficient for processor 60 to configure IMD 16 in the safe mode.

However, in some examples, processor 60 may repeat these steps with the third Hall sensor to reconfirm the presence of the magnetic field. Processor 60 may instruct magnetic field detection circuit 73 to couple a third Hall sensor to the chopper-amplifier and receive the digital value for the third Hall sensor. Processor 60 may compare the received digital value for the third Hall sensor with a baseline measurement for the third Hall sensor. If the absolute value of the difference is greater than a third threshold (different than or same as the first and/or second threshold), processor 60 may reconfirm that a magnetic field is present.

After processor 60 determines or determines and confirms the presence of the magnetic field, processor 60 may configure IMD 16 into safe mode. In safe mode, the presence of the magnetic field may not impact the circuitry of IMD 16. To configure IMD 16 into safe mode, processor 60 may cause switching module 68 to disconnect (e.g., decouple) both stimulation generator 64 and sensing module 66 from leads 20A, 20B so that no current from generated from the magnetic field can flow into IMD 16. In addition, processor 60 may cause switch module 68 to couple electrodes 24, 26 to ground to minimize charge build up on electrodes 24, 26. Processor 60 need not necessarily perform all of these example operations to place IMD 16 into safe mode and there may be additional operations that processor 60 may perform to place IMD 16 into safe mode.

While IMD 16 is in safe mode, processor 60 may configure magnetic field detection circuit 73 to couple one of the first, second, or third Hall sensors to the chopper-amplifier and processor 60 the may receive the resulting digital value. Processor 60 compares the received digital value to respective baseline measurement for the first, second, or third Hall sensor. If the absolute value of the differences between the received digital value and respective baseline measurement for the first, second, and/or third Hall sensors is less than or equal to the respective threshold, processor 60 may determine that the magnetic field is no longer present. In some examples, processor 60 may confirm that there is no magnetic field based on the measurement from one or more of the other Hall sensor other than the Hall sensor used to determine that the magnetic field is no longer present.

After processor 60 determines or determines and confirms that there is no magnetic field, processor 60 may configure IMD 16 into normal mode of operation. In normal mode of operation, IMD 16 is configured to deliver therapy and sense signals as applicable. For instance, in normal mode of operation, switch module 68 may selectively couple stimulation generator 64 and sensing module 66 to electrodes 24, 26 for therapy delivery and sensing.

In the above examples, to determine and confirm the presence of the magnetic field and determine and confirm that the magnetic field is no longer present, processor 60 is described as causing magnetic field detection circuit 73 to selectively couple the first, second, and third Hall sensors to the chopper-amplifier. In some examples, rather than using only one magnetic field detection circuit 73, there may two or more magnetic field detection circuits. Each of these magnetic field detection circuits may be coupled to respective ones of the first, second, and third Hall sensors. In such examples, processor 60 may receive the outputs from the one or more of the magnetic field detection circuits to determine and confirm the presence of the magnetic field and determine and confirm that the magnetic field is no longer present. Accordingly, the configuration of magnetic field detection circuit 73 and processor 60, as illustrated in FIG. 2, is provided merely as one example and should not be considered limiting.

Figure 3:
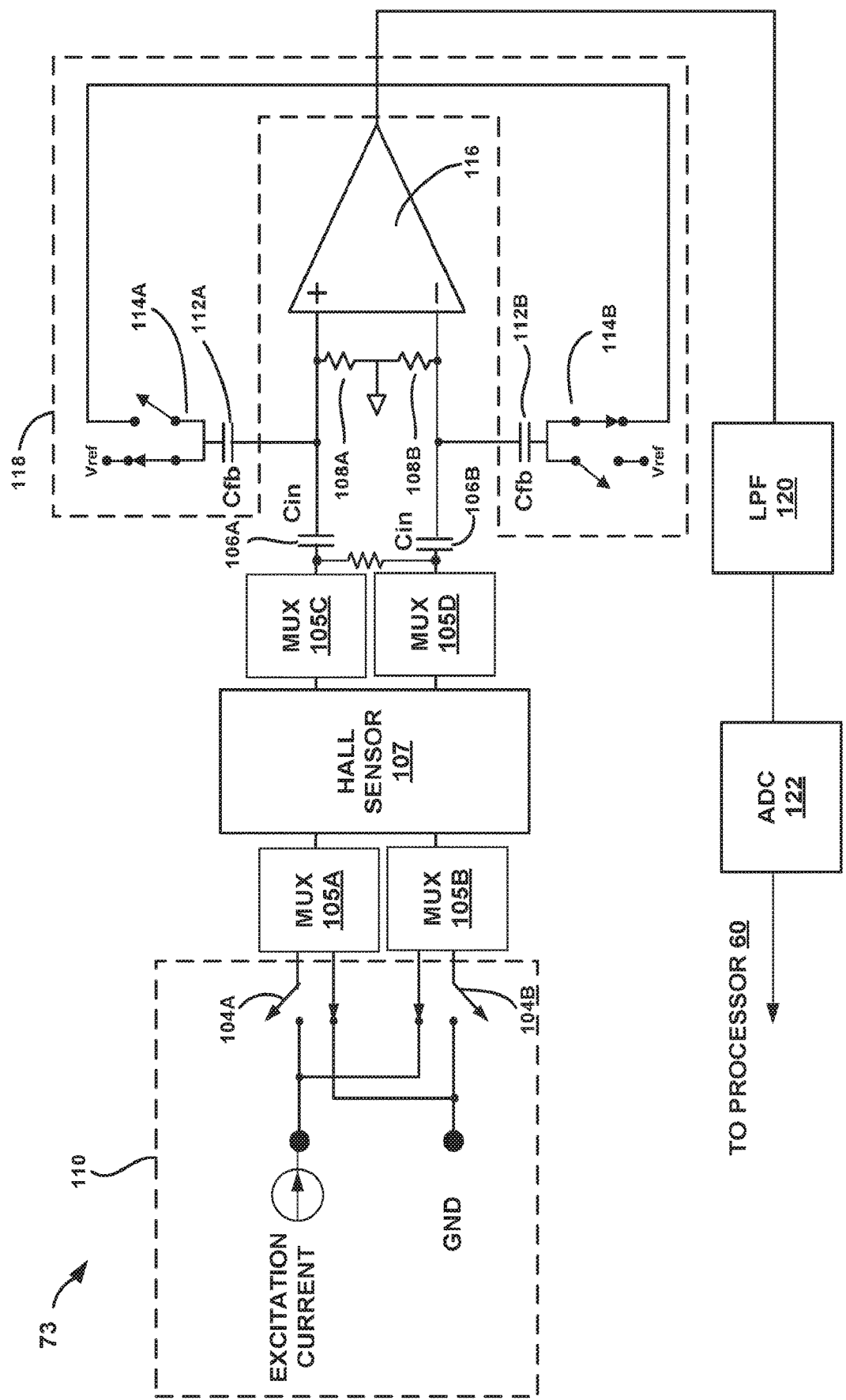
FIG. 3 is a circuit diagram illustrating an example of a magnetic field detection circuit.

FIG. 3 is a circuit diagram illustrating an example of magnetic field detection circuit 73. As illustrated, magnetic field detection circuit 73 includes front end 110, multiplexers (MUXes) 105A, 105B, Hall sensor 107, MUXes 105C, 105D, capacitors 106A, 106B, capacitors 112A, 112B, mixer amplifier 116, feedback path 118, low pass filter (LPF) 120, and analog-to-digital converter (ADC) 122. The combination of front end 110 and mixer amplifier 116 together form a chopper-amplifier that amplify the voltage generated across Hall sensor 107.

In general, the chopper-amplifier operation includes modulating a low frequency (almost DC) signal with a high frequency carrier (e.g., chopper frequency). Once the modulated signal is amplified, the amplified signal is synchronously demodulated with the same chopper frequency. The demodulated-amplified signal includes a high frequency component and a low frequency component, which is low pass filtered to obtain the signal of interest (DC).

In the example illustrated in FIG. 3, front end 110 may be configured to output a modulated voltage generated by Hall sensor 107, if a magnetic field perpendicular to Hall sensor 107 is present, that is fed into mixer amplifier 116 that both amplifies and demodulates the amplified signal. Hall sensor 107 may be one of the first, second, or third Hall sensors (e.g., Z-plane, Y-plane, or X-plane Hall sensors). MUXes 105A, 105B may selectively couple a first pair of terminals of Hall sensor 107 to the excitation current source of front end 110, and MUXes 105C, 105D may selectively couple a second pair of terminals of Hall sensor 107 to the input of mixer amplifier 116.

The excitation current source of front end 110 and the ground voltage level (e.g., 0V) of front end 110 are connected to Hall sensor 107 through switches 104A and 104B (collectively referred to as "switches 104), respectively. Switches 104 are driven by a clock signal provided by a system clock (not shown) and are cross-coupled to each other to reject common-mode signals.

Switches 104 toggle between an open state and a closed state in which the excitation current source is coupled to MUXes 105A, 105B at a clock frequency to modulate (chop) the output of the excitation current source to the carrier (clock) frequency. The excitation current source may output a low frequency current (e.g., DC current) with a low amplitude (e.g., 10 microamps to 100 microamps). The carrier frequency may switch the current at a certain frequency (e.g., within a range of approximately 3 kHz to approximately 10 kHz).

For magnetic field detection, processor 60 may cause MUXes 105A, 105B to couple front end 110 to Hall sensor 107 and MUXes 105C, 105D to couple Hall sensor 107 to mixer amplifier 116. In particular, processor 60 may cause MUXes 105A, 105B to couple to stimulation terminals of Hall sensor 107 (e.g., two of the four terminals) and cause MUXes 105C, 105D to couple to measurement terminals of Hall sensor 107 (e.g., the other two of the four terminals). The stimulation terminals are referred to as a first stimulation terminal and a second stimulation terminal, and the measurement terminals are referred to as a first measurement terminal and a second measurement terminals.

In this example, in a first clock phase, switches 104 toggle in-phase with one another to provide the excitation current from the excitation current source through the first stimulation terminal and second stimulation terminal. In a second clock phase, switches 104 toggle in-phase with one another to provide the excitation current from the excitation current source through the second stimulation terminal and the first stimulation terminal.

During each clock phase, the flow of current through the first and second stimulation terminal or vice-versa and the presence of a magnetic field causes a voltage to be generated across the first and second measurement terminals of Halls sensor 107. The voltage generated across the first and second measurement terminals of Hall sensor 107 is a combination of the voltage caused by the magnetic field and the Hall sensor DC offset of Hall sensor 107.

If the excitation current were to flow through Hall sensor 107 without being chopped by switches 104 at the modulation frequency, then the voltage across Hall sensor 107 would be a DC voltage across the first and second measurement terminals. However, because switches 104 chops the excitation current, Hall sensor 107 generates a chopped voltage signal, at the modulation frequency, that mixer amplifier 116 then receives and amplifies. For example, during the first clock phase, mixer amplifier, via capacitors 106A, 106B, receives a positive voltage across the first and second measurement terminals of Hall sensor 107. During the second clock phase, mixer amplifier 116, via capacitors 106A, 106B, receives a negative voltage across the second and first measurement terminals of Hall sensor 107.

Capacitors 106 are coupled at one end to a corresponding one of MUXes 105C, 105D and to a corresponding input of mixer amplifier 116 at the other end. In particular, capacitor 106A is coupled to the positive input of mixer amplifier 116, and capacitor 106B is coupled to the negative input of amplifier 116, providing a differential input.

Resistors 108A and 108B (collectively referred to as "resistors 108") provide a DC conduction path that controls the voltage bias at the input of mixer amplifier 116. In other words, resistors 108 may be selected to provide an equivalent resistance that is used to keep the bias impedance high. Resistors 108 may, for example, be selected to provide a 5 GΩ equivalent resistor, but other equivalent resistance is possible. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF.

Resistors 108 are merely exemplary and serve to illustrate one of many different biasing schemes for controlling the signal input to mixer amplifier 116. In general, the time constant of resistor 108 and input capacitor 106 may be selected to be approximately 100 times longer than the reciprocal of the chopping frequency.

Mixer amplifier 116 may produce noise and offset in the differential signal applied to its inputs. For this reason, the differential input signal (e.g., the voltage across the first and second measurement terminals of Hall sensor 107) is chopped via switches 104A, 104B and capacitors 106A, 106B to place the signal of interest in a different frequency band from the noise and offset. Then, mixer amplifier 116 chops the amplified signal a second time to demodulate the signal of interest down to baseband while modulating the noise and offset up to the chop frequency band. Mixer amplifier 116 and feedback path 118 process the noisy modulated input signal to achieve a stable measurement indicative of the magnetic level while operating at low power.

In some examples, operating at low power tends to limit the bandwidth of mixer amplifier 116 and creates distortion (ripple) in the output signal. Mixer amplifier 116 and feedback path 118 substantially eliminate the dynamic limitations of chopper stabilization through a combination of chopping at low-impedance nodes and AC feedback, respectively.

In FIG. 3, mixer amplifier 116 is represented with the circuit symbol for an amplifier in the interest of simplicity. However, it should be understood that mixer amplifier 116 may be implemented in accordance with the various circuit diagrams, such as the example provided in FIG. 4. Consequently, mixer amplifier 116 provides synchronous demodulation with respect to front end 110 and substantially eliminates 1/f noise, popcorn noise, and offset from the signal (e.g., voltage generated across first and second measurement terminals of Hall sensor 107) to output a signal that is an amplified representation of the differential voltage produced across the first and second measurement terminals of Hall sensor 107.

Without the negative feedback provided by feedback path 118, the output of mixer amplifier 116 may include spikes superimposed on the desired signal because of the limited bandwidth of the amplifier at low power. However, the negative feedback provided by feedback path 118 suppresses these spikes so that the output of mixer amplifier 116 in steady state is an amplified representation of the differential voltage produced across the first and second measurement terminals of Hall sensor 107 with very little noise.

Feedback path 118 in FIG. 3 may include two feedback paths that provide a differential-to-single ended interface. The top feedback path branch modulates the output of mixer amplifier 116 to provide negative feedback to the positive input terminal of mixer amplifier 116. The feedback path branch includes capacitor 112A and switch 114A. Similarly, the bottom feedback path branch of feedback path 118 includes capacitor 112B and switch 114B that modulate the output of mixer amplifier 116 to provide negative feedback to the negative input terminal of mixer amplifier 116. Capacitors 112A and 112B are connected at one end to switches 114A and 114B, and at the other end to the positive and negative input terminals of mixer amplifier 116, respectively.

Switches 114A and 114B toggle between a reference voltage (Vref) and the output of mixer amplifier 116 to place a charge on capacitors 112A and 112B, respectively. The reference voltage may be, for example, a mid-rail voltage between a maximum rail voltage of amplifier 116 and ground. For example, if the amplifier circuit is powered with a source of 0 to 2 volts, then the mid-rail Vref voltage may be on the order of 1 volt or slightly lower than 1 volt for circuit biasing if needed. In FIG. 3, switches 114A and 114B may be 180 degrees out of phase with each other to ensure that a negative feedback path exists during each half of the clock cycle. One of switches 114 should also be synchronized with mixer amplifier 116 so that the negative feedback suppresses the amplitude of the input signal to mixer amplifier 116 to keep the signal change small in steady state. By keeping the signal change small and switching at low impedance nodes of mixer amplifier 116 (e.g., as shown in the circuit diagram of FIG. 4), the only significant voltage transitions occur at switching nodes. Consequently, glitching (ripples) is substantially eliminated or reduced at the output of mixer amplifier 116.

Switches 104 and 114, as well as the switches at low impedance nodes of mixer amplifier 116, may be CMOS SPDT switches. CMOS switches provide fast switching dynamics that enables switching to be viewed as a continuous process. The transfer function through mixer amplifier 116 with the feedback path 118 may be defined by the transfer function provided in equation (1) below, where Vout is the voltage of the output of mixer amplifier 116, Cin is the capacitance of input capacitors 106, ΔVin is the differential voltage at the inputs to mixer amplifier 116 (e.g., the voltage across Hall sensor 107), Cfb is the capacitance of feedback capacitors 112, and Vref is the reference voltage that switches 114 mix with the output of mixer amplifier 116.

$$Vout = Cin(\Delta Vin)/Cfb + Vref \quad (1)$$

From equation (1) above, the gain of mixer amplifier 116 with the feedback path 118 is set by the ratio of input capacitors Cin and feedback capacitors Cfb (i.e., capacitors 106 and capacitors 112). The ratio of Cin/Cfb may be selected to be on the order of 100. Capacitors 112 may be poly-poly, on-chip capacitors or other types of MOS capacitors and should be well matched.

The output of amplifier 116 is coupled to LPF 120. LPF 120 low pass filters the output of amplifier 116 to filter out the high frequency band of the output from mixer amplifier 116 to keep the value of interest (e.g., low frequency value indicative of the magnetic field plus the amplification of the Hall sensor DC offset). The output of LPF 120 is an analog value that can be used to determine the presence of a magnetic field. ADC 122 converts the analog value into a digital value so that processor 60 can use the digital value for comparison and detection of magnetic field. In some examples, ADC 122 is an incremental ADC, such as high-accuracy oversampled delta-sigma ADC.

In the example techniques described in this disclosure, during manufacturing or post-implant when there is no magnetic field, processor 60 may control MUXes 105A, 105B, 105C, and 105D to couple front end 110 and mixer amplifier 116 to a first Hall sensor. In this case, Hall sensor 107 is the first Hall sensor. Processor 60 may cause the clock system to toggle switches 104 and 114 to cause mixer amplifier 116 to receive the modulated voltage generated across the first and second measurement terminals of the first Hall sensor caused by modulating the current into the first Hall sensor. Mixer amplifier 116 may amplify and demodulate the modulated voltage. LPF 120 low pass filters the output of amplifier 116 and ADC 122 converts the output of LPF 120 into a digital value. Accordingly, LPF 120 and ADC 122 together convert the demodulated signal that mixer amplifier 116 outputs into a value representing an amplitude of the demodulated signal (e.g., a digital value in this example). In examples where digital conversion is not needed, the output of mixer amplifier 116 or a low pass filtered version of the output of mixer amplifier 116 may be a value representing an amplitude of the demodulated signal.

Processor 60 receives the digital value from ADC 122 and stores the value as a baseline measurement for the first Hall sensor. Processor 60 may repeat these steps with the second and third Hall sensors, and store the resulting values as baseline measurements for the second and third Hall sensors when there is no magnetic field.

During operation of IMD 16, processor 60 may cause MUXes 105A, 105B, 105C, and 105D to periodically couple the first Hall sensor (e.g., Hall sensor 107 is the first Hall sensor) to front end 110 and mixer amplifier 116. Processor 60 receives the output from ADC 122 and compares the received digital value with the baseline measurement for the first Hall sensor to determine whether a magnetic field is present.

When the first Hall sensor is coupled to front end 110 and mixer amplifier 116, the excitation current flows through the first and second stimulation terminals, during a first clock phase, and then through the second and first stimulation terminals, during a second clock phase. The flow of current causes a voltage to be generated across the first and second measurement terminals.

If the absolute value of the difference in the received digital value and the baseline measurement is greater than a first threshold, processor 60 may determine that there is a possibility that a magnetic field is present. In some examples, processor 60 may determine that a magnetic field is possibly present without causing the excitation current to flow through the first and/or second stimulation terminals and without relying on the voltage generated across the first and second measurement terminals. For example, MUXes 105A, 105B may not couple front end 110 to the first and/or second measurement terminals of the first Hall sensor, and MUXes 105C, 105D may not couple mixer amplifier 116 to first and/or second stimulation terminals.

Processor 60 may utilize the determination that a magnetic field is present to cause IMD 16 to enter a safe mode of operation. However, in some examples, processor 60 may first confirm and possibly reconfirm the presence of the magnetic field. For instance, processor 60 may cause MUXes 105A, 105B to couple the second Hall sensor (e.g., Hall sensor 107 is the second Hall sensor) to front end 110 and cause MUXes 105C and 105D to couple the second Hall sensor to mixer amplifier 116.

Similar to with the first Hall sensor, processor 60 may determine whether the absolute value of the difference in the received digital value when Hall sensor 107 is the second Hall sensor and the baseline measurement for the second Hall sensor is greater than a second threshold. If the difference is greater than the second threshold, processor 60 may confirm that the magnetic field is present. In response, processor 60 may cause IMD 16 to enter a safe mode of operation.

In some examples, processor 60 reconfirm the presence of the magnetic field by performing similar operations before causing IMD 16 to enter a safe mode. For example, processor 60 may determine whether the difference in the absolute value between the received digital value when Hall sensor 107 is the third Hall sensor and the baseline measurement for the third Hall sensor is greater than a third threshold. If the difference is greater than the third threshold, processor 60 may reconfirm that the magnetic field is present. In response, processor 60 may cause IMD 16 to enter a safe mode of operation.

Once in safe mode, processor 60 may periodically determine whether the magnetic field is no longer present. For example, processor 60 may cause MUXes 105A, 105B to couple one of the Hall sensors (e.g., does not necessarily have to be the first Hall sensor used for determining the presence of the magnetic field) to front end 110 and cause MUXes 105C, 105D to couple this Hall sensor to mixer amplifier. If the absolute difference between the received digital value is less than or equal to the corresponding threshold, processor 60 may determine that the magnetic field is no longer present and cause IMD 16 to return to normal mode. In some examples, processor 60 may confirm and/or reconfirm that the magnetic field is no longer present by receiving digital values when the other Hall sensors are couples by MUXs 105 as Hall sensor 107 and comparing the received digital values to their respective baseline measurements.

In this way, processor 60 may use the first Hall sensor as a trigger for magnetic field detection. Processor 60 may periodically determine whether there is a possibility that a magnetic field is present based on the voltage generated on the first Hall sensor (e.g., by comparing the digital value generated by ADC 122 to a baseline measurement for the first Hall sensor). Processor 60 may cause IMD 16 to enter a safe mode of operation based on the determination of a magnetic field from the voltage generated by the first Hall sensor. As one example, based on the determination that the magnetic field is present, processor 60 may confirm and/or reconfirm the presence of the magnetic field using the second and third Hall sensors.

If, however, the absolute difference in the output of ADC 122 when the first Hall sensor is Hall sensor 107 and the baseline measurement for the first Hall sensor is less than or equal to the first threshold, processor 60 may not cause IMD 16 to enter a safe mode and keep periodically polling (e.g., periodically comparing output from ADC 122 when Hall sensor 107 is the first Hall sensor to the baseline measurement of the first Hall sensor) to determine whether a magnetic field is present. In some examples, the measurements from the first Hall sensor may indicate that there is a possibility of a magnetic field, but processor 60 may not have confirmed or reconfirmed the presence of the magnetic field based on measurements from the second and/or third Hall sensors. In such examples, processor 60 may keep periodically polling the measurement from the first Hall sensor. However, processor 60 may increase the period at which it polls the measurement from the first Hall sensor so as to avoid repeatedly triggering the measurement from the second and/or third Hall sensors.

Figure 4:
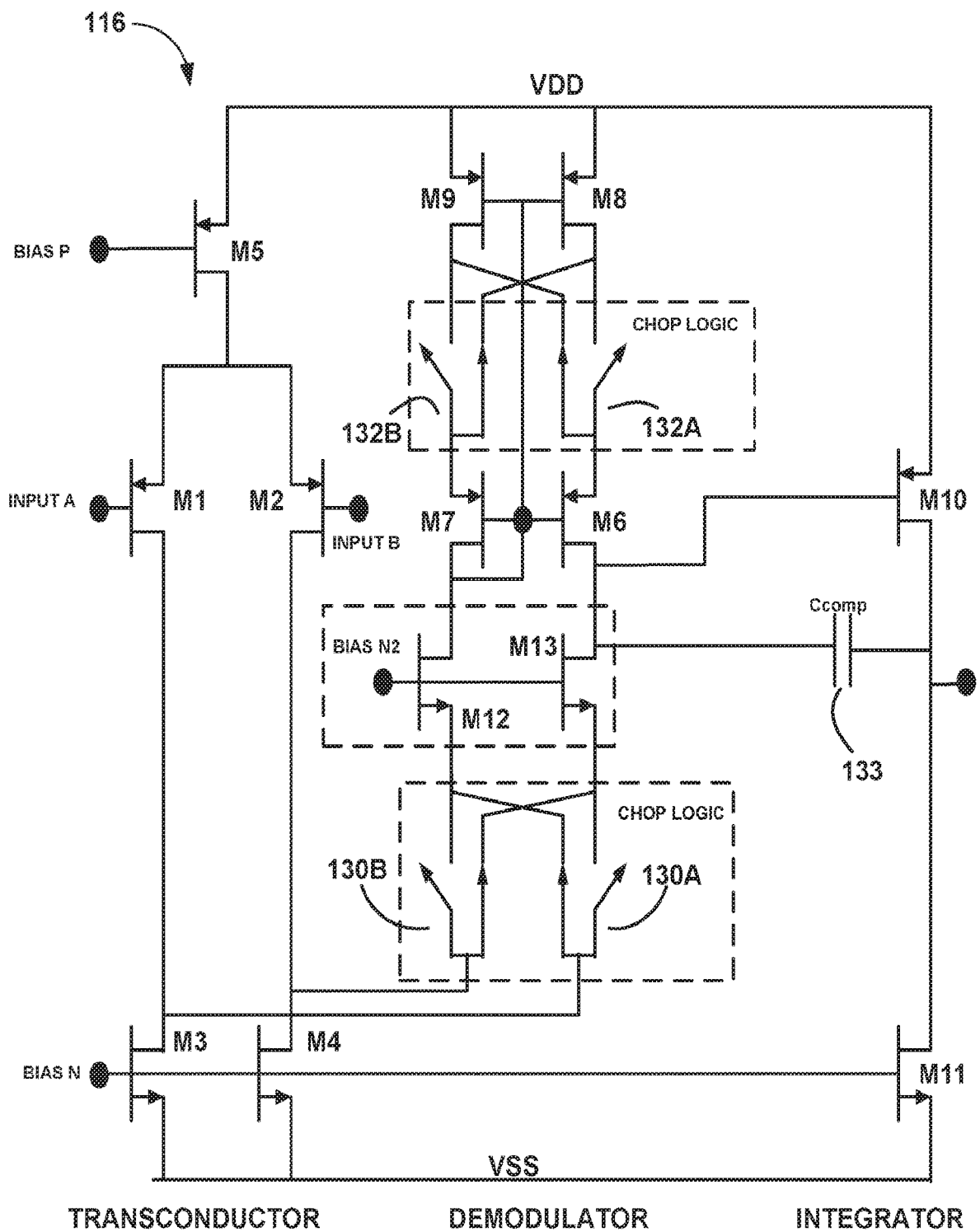
FIG. 4 is a circuit diagram illustrating a chopper-stabilized mixer amplifier forming part of a magnetic field detection circuit.

FIG. 4 is a circuit diagram illustrating chopper-stabilized mixer amplifier 116 forming part of magnetic field detection circuit 73. As previously described, mixer amplifier 116 amplifies a noisy modulated input signal (e.g., voltage generated across first and second measurement terminals of Hall sensor 107) to produce an amplified signal and demodulates the amplified signal. Mixer amplifier 116 also substantially eliminates noise from the demodulated signal to generate an output signal that LPF 120 receives. In the example of FIG. 4, mixer amplifier 116 is a modified folded-cascode amplifier with switching at low impedance nodes. The modified folded-cascode architecture allows the currents to be partitioned to maximize noise efficiency. In general, the folded cascode architecture is modified in FIG. 4 by adding two sets of switches. One set of switches is illustrated in FIG. 4 as switches 130A and 130B (collectively referred to as "switches 130") and the other set of switches includes switches 132A and 132B (collectively referred to as "switches 132").

Switches 130 are driven by chop logic to support the chopping of the amplified signal for demodulation at the chop frequency. In particular, switches 130 demodulate the amplified signal and modulate front-end offsets and 1/f noise. Switches 132 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The output of amplifier 116 is at baseband, allowing an integrator formed by transistor M10 and capacitor 133 (Ccomp) to stabilize feedback path 118 (not shown in FIG. 4) and filter modulated offsets. For example, the integrator formed by transistor M10 and Ccomp capacitor 133 is an example of LPF 120 of FIG. 3.

Mixer amplifier 116 may include three blocks: a transconductor, a demodulator, and an integrator. The core is similar to a folded cascode. In the transconductor section, transistor M5 is a current source for the differential pair of input transistors M1 and M2. In some examples, transistor M5 may pass approximately 800 nA, which is split between transistors M1 and M2, e.g., 400 nA each. Transistors M1 and M2 are the inputs to amplifier 116. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 130 alternate the current back and forth between the legs of the demodulator to demodulate the measurement signal back to baseband, while the offsets from the transconductor are up-modulated to the chopper frequency. Transistors M6, M7, M8 and M9 form a self-biased cascode mirror, and make the signal single-ended before passing into the output integrator formed by transistor M10 and capacitor 133 (Ccomp). Switches 132 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 66 suppressed.

The output DC signal current and the upmodulated error current pass to the integrator, which is formed by transistor M10, capacitor 133, and the bottom NFET current source transistor M11. Again, this integrator serves to both stabilize the feedback path and filter out the upmodulated error sources. The bias for transistor M10 may be approximately 100 nA, and is scaled compared to transistor M8. The bias for low side NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 4 may be field effect transistors (FETs), and more particularly CMOS transistors.

Figure 5A:
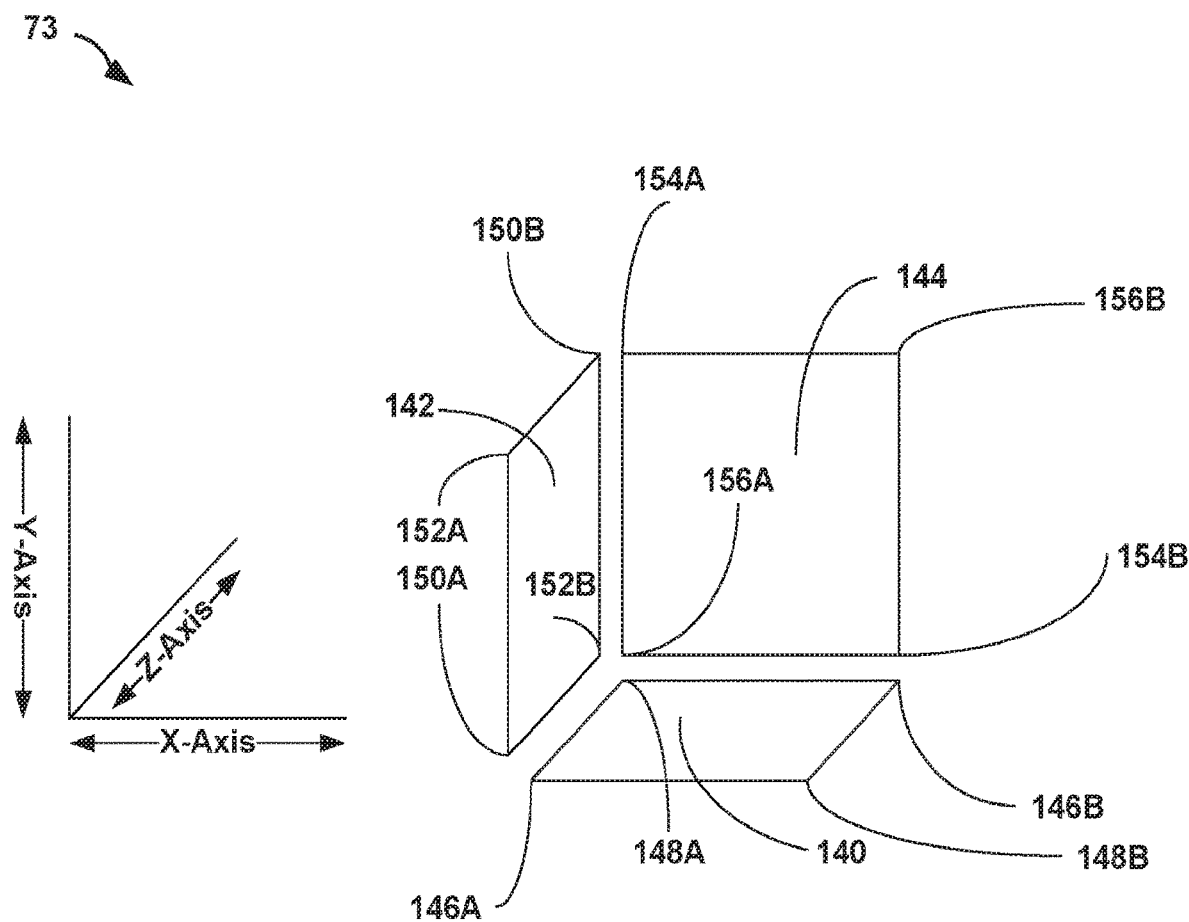
FIG. 5A is a block diagram illustrating an example Hall sensor configuration forming part of a magnetic field detection circuit.

FIG. 5A is a block diagram illustrating an example Hall sensor configuration forming part of magnetic field detection circuit 73. As illustrated in FIG. 5A, magnetic field detection circuit 73 includes first Hall sensor 140, second Hall sensor 142, and third Hall sensor 144. First Hall sensor 140 (e.g., Z-plane Hall sensor) resides along the Z and X-axis. The Z-axis is the dorsal-ventral axis of patient 12, and the X-axis is the lateral-medial axis of patient 12. Second Hall sensor 142 (e.g., Y-plane Hall sensor) resides along the Y and Z-axis. The Y-axis is the superior-inferior axis of patient 12. Third Hall sensor 144 resides along the X and Y-axis. In general, first Hall sensor 140 resides in a first plane, second Hall sensor 142 resides in a second plane orthogonal to the first plane, and third Hall sensor 144 resides in a third plane orthogonal to both the first and second planes.

There may be various ways in which to form first Hall sensor 140, second Hall sensor 142, and third Hall sensor 144. Various example ways are described in U.S. Pat. No. 8,750,961, issued Jun. 10, 2014, and assigned to Medtronic, Inc. There may various other ways in which to form first Hall sensor 140, second Hall sensor 142, and third Hall sensor 144.

Each of first Hall sensor 140, second Hall sensor 142, and third Hall sensor 144 includes pairs of stimulation terminals and pairs of measurement terminals. For example, first Hall sensor 140 includes stimulation terminals 146A, 146B and measurement terminals 148A, 148B. Second Hall sensor 142 includes stimulation terminals 150A, 150B and measurement terminals 152A, 152B. Third Hall sensor 144 includes stimulation terminals 154A, 154B and measurement terminals 156A, 156B.

In one or more examples described in this disclosure, to determine the presence of a magnetic field, determine that the magnetic field is no longer present, and/or to determine the baseline measurement of first Hall sensor 140, processor 60 may cause MUXes 105A, 105B to couple stimulation terminals 146A, 146B of first Hall sensor 140 to front end 110 to allow the excitation current to flow from stimulation terminal 146A to stimulation terminal 146B in a first clock phase and from stimulation terminal 146B to stimulation terminal 146A in a second clock phase. Processor 60 may cause MUXes 105C, 105D to couple measurement terminals 148A, 148B to the input of mixer amplifier 116. In this example, processor 60 may not cause MUXes 105A, 105B to couple measurement terminals 148A, 148B to front end 110 or couple stimulation terminals 146A, 146B to the input of mixer amplifier 116.

To confirm the presence of the magnetic field, determine that the magnetic field is no longer present, and/or to determine the baseline measurement of second Hall sensor 142, processor 60 may cause MUXes 105A, 105B to couple stimulation terminals 150A, 150B of second Hall sensor 142 to front end 110 to allow the excitation current to flow from stimulation terminal 150A to stimulation terminal 150B in a first clock phase and from stimulation terminal 150B to stimulation terminal 150A in a second clock phase. Processor 60 may cause MUXes 105C, 105D to couple measurement terminals 152A, 152B to the input of mixer amplifier 116. In this example, processor 60 may not cause MUXes 105A, 105B to couple measurement terminals 152A, 152B to front end 110 or couple stimulation terminals 150A, 150B to the input of mixer amplifier 116.

To reconfirm the presence of the magnetic field, determine that the magnetic field is no longer present, and/or to determine the baseline measurement of third Hall sensor 144, processor 60 may cause MUXes 105A, 105B to couple stimulation terminals 154A, 154B of third Hall sensor 144 to front end 110 to allow the excitation current to flow from stimulation terminal 154A to stimulation terminal 154B in a first clock phase and from stimulation terminal 154B to stimulation terminal 154A in a second clock phase. Processor 60 may cause MUXes 105C, 105D to couple measurement terminals 156A, 156B to the input of mixer amplifier 116. In this example, processor 60 may not cause MUXes 105A, 105B to couple measurement terminals 156A, 156B to front end 110 or couple stimulation terminals 154A, 154B to the input of mixer amplifier 116.

Figure 5B:
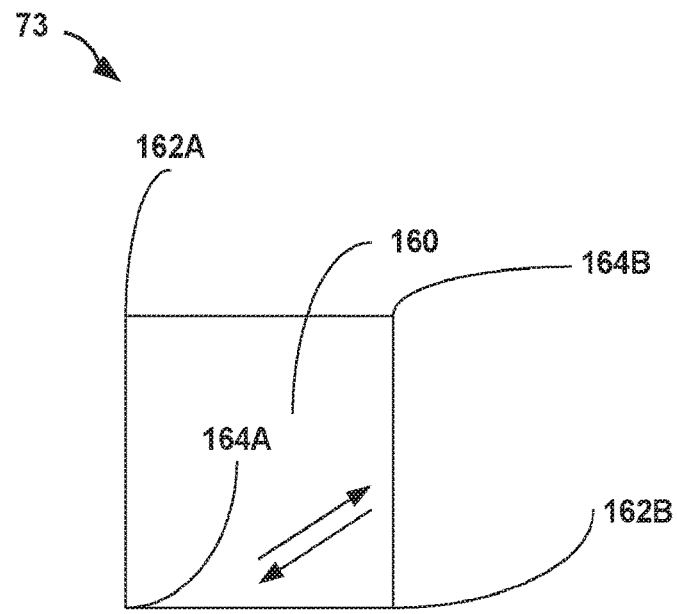
FIG. 5B is a block diagram illustrating another example Hall sensor configuration forming part of a magnetic field detection circuit.
Figure 5B:
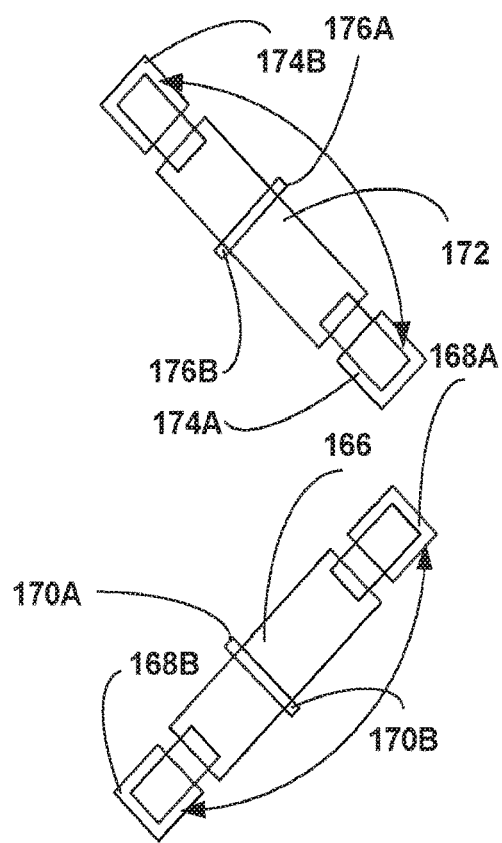

FIG. 5B is a block diagram illustrating another example Hall sensor configuration forming part of a magnetic field detection circuit. As illustrated in FIG. 5B, magnetic field detection circuit 73 includes first Hall sensor 160, second Hall sensor 166, and third Hall sensor 172. First Hall sensor 160 may be the Z-plane Hall sensor. Second Hall sensor 166 and third Hall sensor 172 may be the X-plane Hall sensor and Y-plane Hall sensor, respectively or vice-versa.

In the illustrated example, the arrows illustrate the flow of the excitation current. For example, due to a perpendicular magnetic field (e.g., into and out of the page illustrating FIG. 5B), in the first Hall sensor 160, in response to the current flowing between stimulation terminals 164A, 164B, the voltage is measured across measurement terminals 162A, 162B. Due to a perpendicular magnetic field, for second Hall sensor 166, in response to the current flowing between stimulation terminals 168A, 168B, the voltage is measured across measurement terminals 170A, 170B. Due to a perpendicular magnetic field, for third Hall sensor 172, in response to the current flowing between stimulation terminals 174A, 174B, the voltage is measured across measurement terminals 176A, 176B.

For second Hall sensor 166 and third Hall sensor 172, the current goes into the page from one terminal to other terminal. Second Hall sensor 166 and third Hall sensor 172 are place 45 degrees from the reference, as illustrated. In this case, second Hall sensor 166 and third Hall sensor 172 are 90 degrees from each other.

Figure 6:
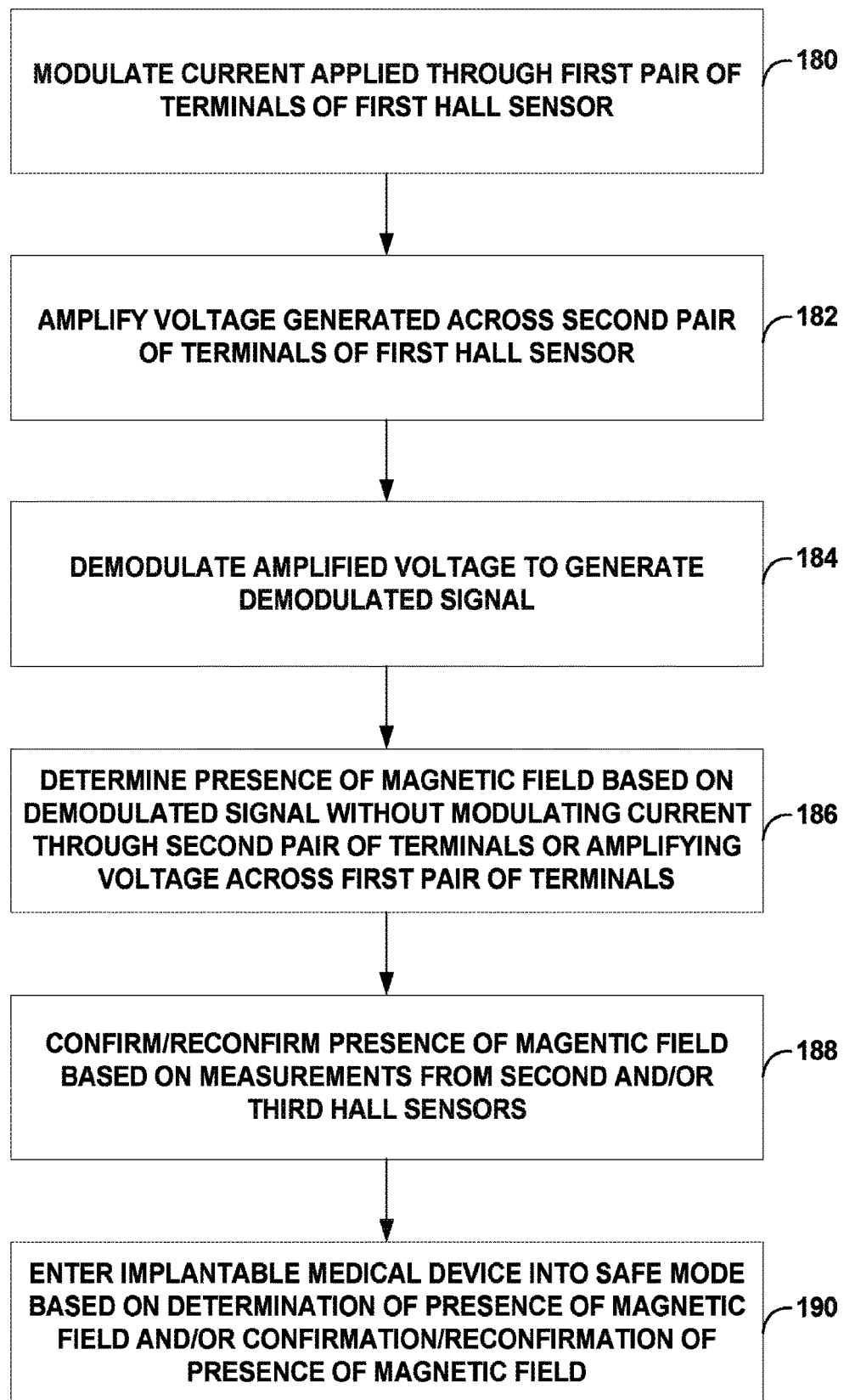
FIG. 6 is a flowchart illustrating an example method of magnetic field detection.

FIG. 6 is a flowchart illustrating an example method of magnetic field detection. The example illustrated in FIG. 6 provides for one way to determine whether patient 12 is within a magnetic field of sufficient strength to potentially impact circuitry of IMD 16. Only for ease of description, the example of FIG. 6 is described with respect to FIG. 5A, but the techniques are applicable to the example illustrated in FIG. 5B.

Based on the example techniques described with respect to FIG. 6, IMD 16 may configure itself into a safe mode (e.g., MRI safe mode). In this example, processor 60 may cause MUXes 105A, 105B to couple a first Hall sensor (e.g., Hall sensor 107 is the first Hall sensor) to front end 110 and MUXes 105C, 105D to couple the first Hall sensor to mixer amplifier 116.

For magnetic field detection, switches 104 of front end 110 of magnetic field detection circuit 73 may modulate an excitation current applied through a first pair of terminals (e.g., first and second terminals) (180). As an example, switches 104 may modulate the excitation current such that the current flows from stimulation terminal 146A to 146B of Hall sensor 140 in a first clock phase and flows from stimulation terminal 146B to 146A of Hall sensor 140 in a second clock phase.

The current being applied through the stimulation terminals 146A, 146B of Hall sensor 140 at least in part causes a voltage to be generated on a second pair of terminals (e.g., third and fourth terminals) of Hall sensor 140. The presence of the magnetic field also contributes to the generation of the voltage across the second pair of terminals. For example, the current flowing through stimulation terminals 146A, 146B may in part cause a voltage to be generated across measurement terminals 148A, 148B. If a magnetic field is present, the magnetic field also contributes to the generation of the voltage across measurement terminals 148A, 148B.

Mixer amplifier 116 amplifies the voltage generated across the second pair of terminals of first Hall sensor 140 (182). For example, mixer amplifier 116 amplifies a voltage across measurement terminals 148A, 148B. Switches 114 together with mixer amplifier demodulate the amplified voltage to generate a demodulated signal (184).

Processor 60 determines presence of a magnetic field based on the demodulated signal without application of excitation current through the second pair of terminals (e.g., the third and fourth terminals or measurement terminals 148A, 148B) and without amplification of voltage across the first pair of terminals (e.g., the first and second terminals or stimulation terminals 146A, 146B) (186). In this way, the techniques may determine presence of a magnetic field without needing to correct for the offset. For example, LPF 120 and ADC 122 together convert the demodulated signal into a value representing an amplitude of the demodulated signal (e.g., a digital value that processor 60 receives). Processor 60 may determine a difference between the value and a baseline measurement for first Hall sensor 140. In this example, processor 60 may determine presence of the magnetic field based on the difference being greater than or less than a threshold (e.g., the absolute value of the difference is greater than a threshold).

For example, the baseline measurement may be a digital value generated during manufacturing when no magnetic field is present. This baseline measurement may include the offset of the Hall sensor and offset from any other component. As one example, the baseline measurement may be a 14 bit digital value. Processor 60 may determine whether there is a difference between the baseline measurement and the measured digital value. For example, assume that the baseline measurement for first Hall sensor 140 is 6450 with 50 microamps excitation current. In this example, 6450 represents the 14 bit digital value is a base 10 value. For example, the digital value for the baseline measurement may be 01100100110010.

If there is a 20 gauss magnetic field present with the same excitation current, then the measured digital value for the first Hall sensor may be approximately 6440 or 6460 based on the polarity of the magnetic field (e.g., 01100100101000 for 6440 or 01100100111100 for 6460). In this example, the absolute value of the difference between the baseline measurement and the measured digital value when 20 gauss is present can be considered to approximately a 10 to 15 LSB shift. Here, the LSB shift is referring to the difference in the base 10 values of the baseline measurement and the measured digital value (e.g., 6450 minus 6440 or 6450 minus 6460). However, the values 6460, 6450, and 6440 are base 10 representations of the digital values.

In this example, if the threshold is less than 10 LSB, then processor 60 may determine that a magnetic field is present. If, however, the threshold is greater than 20 LSB, then processor 60 may not determine that magnetic field is present.

Although processor 60 may determine the presence of the magnetic field based on measurements from first Hall sensor 140, processor 60 may confirm or confirm and reconfirm the presence of the magnetic field based on measurements from second Hall sensor 142 and/or third Hall sensor 144 (188). For example, magnetic field detection circuit 73 and processor 60 may repeat operations similar to those described above such as modulating, amplifying, demodulating, and determining presence of magnetic field based on first Hall sensor 140, but using second Hall sensor 142 and/or third Hall sensor 144 for confirming and/or reconfirming the presence of the magnetic field.

In this example, the baseline measurement for the second and third Hall sensors may be a digital value, respectively, generated during manufacturing when no magnetic field is present. This baseline measurement for each of the second and third Hall sensors may include the offset of the second and third Hall sensors and offset from any other component. Processor 60 may determine whether there is a difference in between the baseline measurement and the measured digital value. For second Hall sensor 142 and third Hall sensor 144, the baseline measurement may be 6160 for a 100 microamp excitation current. For approximately, 400 gauss, the measurement from second Hall sensor 142 and third Hall sensor 144 may be a shift of +20 LSB at 100 microamps based on the polarity of the magnetic field.

If the threshold is set to 20 LSB for second Hall sensor 142 and third Hall sensor 144, then with 400 gauss, processor 60 may confirm that the magnetic field is present. If, however, the threshold is set to greater than 20 LSB for second Hall sensor 142 and third Hall sensor 144, then with 400 gauss, processor 60 may determine that no magnetic field is present. In some examples, the magnetic field for an MIll may be 1.5 to 3 Teslas. Accordingly, the threshold may be closer to 40 LSB for second Hall sensor 142 and third Hall sensor 144 assuming 100 microamps of excitation current and the example baseline measurement.

The thresholds provided above are merely one example to assist with understanding, and different thresholds may be selected on a case by case basis. Similarly, the excitation current amplitudes and the measurement values are provided as an example for understanding purposes and should not be considered as limiting.

Processor 60 may cause IMD 16 to enter into safe mode based at least in part on the determination that the magnetic field is present, and further based on confirmation/reconfirmation that magnetic field is present (190). For instance, because determination of the magnetic field based on measurements from first Hall sensor 140 triggers confirmation and reconfirmation, processor 60 causes IMD 16 to enter into safe mode based in part on the determination of the presence of the magnetic field. In some examples, processor 60 causes IMD 16 to enter into safe mode based on the determination of the presence of the magnetic field and confirmation or confirmation and reconfirmation of the presence of the magnetic field.

After IMD 16 is in the safe mode, processor 60 may determine that a magnetic field is no longer present in a similar manner as above, but determining that a difference in the value representing the amplitude of the demodulates signal and respective baseline measurement is less than or equal to respective thresholds. For example, processor 60 may determine that the magnetic field is no longer present based on voltage generated across one or more of a plurality of Hall sensors (e.g., one or more of first Hall sensor 140, second Hall sensor 142, and third Hall sensor 144).

The techniques described in this disclosure may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), static RAM (SRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method of magnetic field detection, the method comprising:
    modulating, at a frequency, a current applied through first and second terminals of a Hall sensor;
    amplifying a voltage across third and fourth terminals of the Hall sensor to generate an amplified voltage, wherein the voltage is generated at least in part in response to the current being applied through the first and second terminals of the Hall sensor;
    demodulating, at the same frequency, the amplified voltage to generate a demodulated signal;
    determining presence of a magnetic field based on the demodulated signal, wherein the presence of the magnetic field is determined without application of a current through the third and fourth terminals of the Hall sensor and without amplification of a voltage across the first and second terminals; and
    entering an implantable medical device, comprising the Hall sensor, into a safe mode based in part on the determination of the presence of the magnetic field.

2. The method of claim 1, wherein the Hall sensor comprises a first Hall sensor, the method further comprising:
    in response to determining presence of the magnetic field based on the demodulated signal:
        modulating, at the frequency, a current applied through first and second terminals of a second Hall sensor;
        amplifying a voltage across third and fourth terminals of the second Hall sensor to generate an amplified voltage for the second Hall sensor, wherein the voltage across the third and fourth terminals of the second Hall sensor is generated at least in part from the current being applied through the first and second terminals of the second Hall sensor;
        demodulating the amplified voltage for the second Hall sensor to generate a demodulated signal for the second Hall sensor;
        confirming presence of the magnetic field based on the demodulated signal for the second Hall sensor, wherein the presence of the magnetic field is confirmed without application of a current through the third and fourth terminals of the second Hall sensor and without amplification of a voltage across the first and second terminals of the second Hall sensor,
    wherein entering the safe mode comprises entering the safe mode based on both the determination of the presence of the magnetic field and the confirmation of the presence of the magnetic field.

3. The method of claim 2, further comprising:
    in response to confirming presence of the magnetic field based on the demodulated signal for the second Hall sensor:
        modulating, at the frequency, a current applied through first and second terminals of a third Hall sensor;
        amplifying a voltage across third and fourth terminals of the third Hall sensor to generate an amplified voltage for the third Hall sensor, wherein the voltage across the third and fourth terminals of the third Hall sensor is generated at least in part from the current being applied through the first and second terminals of the third Hall sensor;
        demodulating the amplified voltage for the third Hall sensor to generate a demodulated signal for the third Hall sensor;
        reconfirming presence of the magnetic field based on the demodulated signal for the third Hall sensor, wherein the presence of the magnetic field is reconfirmed without application of a current through the third and fourth terminals of the third Hall sensor and without amplification of a voltage across the first and second terminals of the third Hall sensor,
    wherein entering the safe mode comprises entering the safe mode based on the determination of the presence of the magnetic field, the confirmation of the presence of the magnetic field, and the reconfirmation of the presence of the magnetic field.

4. The method of claim 3, wherein the first Hall sensor resides in a first plane, wherein the second Hall sensor resides in a second plane orthogonal to the first plane, and wherein the third Hall sensor resides in a third plane orthogonal to both the first and second planes.

5. The method of claim 1, further comprising:
    converting the demodulated signal into a value representing an amplitude of the demodulated signal; and
    determining an absolute value of a difference between the value and a baseline measurement for the Hall sensor,
    wherein determining presence of the magnetic field comprises determining presence of the magnetic field based on the absolute value of the difference being greater than a threshold.

6. The method of claim 1, wherein the Hall sensor comprises one of a plurality of Hall sensors, the method further comprising:
    determining that the magnetic field is no longer present based on voltage generated across one or more of the plurality of Hall sensors.

7. The method of claim 1, wherein the current comprises an amplitude of approximately 10 microamps to 100 microamps.

8. An implantable medical device (IMD) for magnetic field detection, the IMD comprising:
a Hall sensor;
a magnetic field detection circuit configured to:
modulate, at a frequency, a current applied through first and second terminals of the Hall sensor;
amplify a voltage across third and fourth terminals of the Hall sensor to generate an amplified voltage, wherein the voltage is generated at least in part in response to the current being applied through the first and second terminals of the Hall sensor; and
demodulate, at the same frequency, the amplified voltage to generate a demodulated signal; and processing circuitry configured to:
determine presence of a magnetic field based on the demodulated signal, wherein the presence of the magnetic field is determined without application of a current through the third and fourth terminals of the Hall sensor and without amplification of a voltage across the first and second terminals; and
enter the IMD into a safe mode based in part on the determination of the presence of the magnetic field.

9. The IMD of claim 8, wherein the Hall sensor comprises a first Hall sensor, the IMD further comprising a second Hall sensor, and wherein the magnetic field detection circuit is configured to:
in response to the processing circuitry determining presence of the magnetic field based on the demodulated signal:
modulate, at the frequency, a current applied through first and second terminals of a second Hall sensor;
amplify a voltage across third and fourth terminals of the second Hall sensor to generate an amplified voltage for the second Hall sensor, wherein the voltage across the third and fourth terminals of the second Hall sensor is generated at least in part from the current being applied through the first and second terminals of the second Hall sensor; and
demodulate the amplified voltage for the second Hall sensor to generate a demodulated signal for the second Hall sensor, wherein the processing circuitry is configured to:
confirm presence of the magnetic field based on the demodulated signal for the second Hall sensor, wherein the presence of the magnetic field is confirmed without application of a current through the third and fourth terminals of the second Hall sensor and without amplification of a voltage across the first and second terminals of the second Hall sensor; and
enter the safe mode based on both the determination of the presence of the magnetic field and the confirmation of the presence of the magnetic field.

10. The IMD of claim 9, further comprising:
a third Hall sensor,
wherein in response to the processing circuitry confirming presence of the magnetic field based on the demodulated signal for the second Hall sensor, the magnetic field detection circuitry is configured to:
modulate, at the frequency, a current applied through first and second terminals of the third Hall sensor;
amplify a voltage across third and fourth terminals of the third Hall sensor to generate an amplified voltage for the third Hall sensor, wherein the voltage across the third and fourth terminals of the third Hall sensor is generated at least in part from the current being applied through the first and second terminals of the third Hall sensor; and
demodulate the amplified voltage for the third Hall sensor to generate a demodulated signal for the third Hall sensor, wherein the processing circuitry is configured to:
reconfirm presence of the magnetic field based on the demodulated signal for the third Hall sensor, wherein the presence of the magnetic field is reconfirmed without application of a current through the third and fourth terminals of the third Hall sensor and without amplification of a voltage across the first and second terminals of the third Hall sensor; and
enter the safe mode based on the determination of the presence of the magnetic field, the confirmation of the presence of the magnetic field, and the reconfirmation of the presence of the magnetic field.

11. The IMD of claim 10, wherein the first Hall sensor resides in a first plane, wherein the second Hall sensor resides in a second plane orthogonal to the first plane, and wherein the third Hall sensor resides in a third plane orthogonal to both the first and second planes.

12. The IMD of claim 8, further comprising:
an analog-to-digital converter configured to convert the demodulated signal into a value representing an amplitude of the demodulated signal,
wherein the processing circuitry is configured to:
determine an absolute value of a difference between the value and a baseline measurement for the Hall sensor, and
wherein to determine presence of the magnetic field, the processing circuitry is configured to determine presence of the magnetic field based on the absolute value of the difference being greater than or less than a threshold.

13. The IMD of claim 8, wherein the Hall sensor comprises one of a plurality of Hall sensors, and wherein the processing circuitry is configured to:
determine that the magnetic field is no longer present based on voltage generated across one or more of the plurality of Hall sensors.

14. The IMD of claim 8, wherein the current comprises an amplitude of approximately 10 microamps to 100 microamps.

15. An implantable medical device (IMD) for magnetic field detection, the IMD comprising:
means for modulating, at a frequency, a current applied through first and second terminals of a Hall sensor;
means for amplifying a voltage across third and fourth terminals of the Hall sensor to generate an amplified voltage, wherein the voltage is generated at least in part in response to the current being applied through the first and second terminals of the Hall sensor;
means for demodulating, at the same frequency, the amplified voltage to generate a demodulated signal;
means for determining presence of a magnetic field based on the demodulated signal, wherein the presence of the magnetic field is determined without application of a current through the third and fourth terminals of the Hall sensor and without amplification of a voltage across the first and second terminals; and
means for entering an implantable medical device into a safe mode based in part on the determination of the presence of the magnetic field.

16. The IMD of claim 15, wherein the Hall sensor comprises a first Hall sensor, the device further comprising:
in response to determining presence of the magnetic field based on the demodulated signal:

means for modulating, at the frequency, a current applied through first and second terminals of a second Hall sensor;

means for amplifying a voltage across third and fourth terminals of the second Hall sensor to generate an amplified voltage for the second Hall sensor, wherein the voltage across the third and fourth terminals of the second Hall sensor is generated at least in part from the current being applied through the first and second terminals of the second Hall sensor;

means for demodulating the amplified voltage for the second Hall sensor to generate a demodulated signal for the second Hall sensor;

means for confirming presence of the magnetic field based on the demodulated signal for the second Hall sensor, wherein the presence of the magnetic field is confirmed without application of a current through the third and fourth terminals of the second Hall sensor and without amplification of a voltage across the first and second terminals of the second Hall sensor, wherein the means for entering the safe mode comprises means for entering the safe mode based on both the determination of the presence of the magnetic field and the confirmation of the presence of the magnetic field.

17. The IMD of claim 16, further comprising:

in response to confirming presence of the magnetic field based on the demodulated signal for the second Hall sensor:

means for modulating, at the frequency, a current applied through first and second terminals of a third Hall sensor;

means for amplifying a voltage across third and fourth terminals of the third Hall sensor to generate an amplified voltage for the third Hall sensor, wherein the voltage across the third and fourth terminals of the third Hall sensor is generated at least in part from the current being applied through the first and second terminals of the third Hall sensor;

means for demodulating the amplified voltage for the third Hall sensor to generate a demodulated signal for the third Hall sensor;

means for reconfirming presence of the magnetic field based on the demodulated signal for the third Hall sensor, wherein the presence of the magnetic field is reconfirmed without application of a current through the third and fourth terminals of the third Hall sensor and without amplification of a voltage across the first and second terminals of the third Hall sensor, wherein the means for entering the safe mode comprises means for entering the safe mode based on the determination of the presence of the magnetic field, the confirmation of the presence of the magnetic field, and the reconfirmation of the presence of the magnetic field.

18. The IMD of claim 17, wherein the first Hall sensor resides in a first plane, wherein the second Hall sensor resides in a second plane orthogonal to the first plane, and wherein the third Hall sensor resides in a third plane orthogonal to both the first and second planes.

19. The IMD of claim 15, further comprising:

means for converting the demodulated signal into a value representing an amplitude of the demodulated signal; and means for determining an absolute value of a difference between the value and a baseline measurement for the Hall sensor, wherein the means for determining presence of the magnetic field comprises means for determining presence of the magnetic field based on the absolute value of the difference being greater than or less than a threshold.

20. The IMD of claim 15, wherein the Hall sensor comprises one of a plurality of Hall sensors, the IMD further comprising:

means for determining that the magnetic field is no longer present based on voltage generated across one or more of the plurality of Hall sensors.

21. The IMD of claim 15, wherein the current comprises an amplitude of approximately 10 microamps to 100 microamps.

* * * * *